(12) United States Patent
Addington et al.

(10) Patent No.: US 8,394,434 B2
(45) Date of Patent: *Mar. 12, 2013

(54) SCF EXTRACT CONTAINING CARDIAC GLYCOSIDE

(75) Inventors: Otis Crandell Addington, San Antonio, TX (US); Feng Zhang, Burlingame, CA (US); John J. Koleng, Austin, TX (US)

(73) Assignee: Phoenix Biotechnology, Inc., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/417,686

(22) Filed: Mar. 12, 2012

(65) Prior Publication Data

US 2012/0219620 A1    Aug. 30, 2012

Related U.S. Application Data

(60) Division of application No. 12/019,435, filed on Jan. 24, 2008, now Pat. No. 8,187,644, which is a continuation-in-part of application No. PCT/US2006/029061, filed on Jul. 26, 2006, which is a continuation-in-part of application No. 11/191,650, filed on Jul. 28, 2005, now Pat. No. 7,402,325.

(51) Int. Cl.
*A61K 36/13* (2006.01)
*A61K 36/00* (2006.01)

(52) U.S. Cl. ........................ 424/770; 424/725
(58) Field of Classification Search .................. None
See application file for complete search history.

(56) References Cited

U.S. PATENT DOCUMENTS

| | | | |
|---|---|---|---|
| 3,833,472 A | 9/1974 | Yamauchi | |
| 4,554,170 A | 11/1985 | Panzner et al. | |
| 4,816,259 A * | 3/1989 | Matthews et al. | 424/463 |
| 4,968,787 A | 11/1990 | Inada et al. | |
| 5,135,745 A * | 8/1992 | Ozel | 424/725 |
| 5,236,132 A | 8/1993 | Rowley, Jr. | |
| 5,598,979 A | 2/1997 | Rowley, Jr. | |
| 5,837,831 A | 11/1998 | Gruning et al. | |
| 5,869,060 A | 2/1999 | Yoon et al. | |
| 6,451,339 B2 | 9/2002 | Patel et al. | |
| 6,517,015 B2 | 2/2003 | Rowley, Jr. | |
| 6,565,897 B2 | 5/2003 | Selvaraj et al. | |
| 6,715,705 B2 | 4/2004 | Rowley, Jr. | |
| 6,737,552 B1 | 5/2004 | Crombie | |
| 7,402,325 B2 | 7/2008 | Addington | |
| 8,187,644 B2 | 5/2012 | Addington | |
| 2004/0082521 A1 | 4/2004 | Singh | |
| 2005/0112059 A1 | 5/2005 | Newman et al. | |

OTHER PUBLICATIONS

Food Science Tech. Int. (2002), vol. 8, (5), pp. 269-284, "Applications and Possibilities of Supercritical CO2 Extraction in Food Processing Industry: An Overview".*
Wenli et al. ("Supercritical CO2 extraction of resveratrol and its glycoside piceid from Chinese traditional medicinal herb *Polygonum cuspidatum*", J. Sci. Food Agric. (2005), 85(3), 489-492).
Farrukh et al. ("Inhibition of 12-O-tetradecanoylphorbol-13-acetate-induced tumor promotion markers in CD-1 mouse skin by oleandrin", Toxicology Appl. Pharmacol. (2004), 195, 361-369).
Raventos M, Durate S, Alarcon R. Application and Possibilities of Supercritical CO2 Extraction in Food Processing Industry: An Overview. Food Sci. Tech. Int. vol. 8 (5) (2002) 269-284.

* cited by examiner

*Primary Examiner* — Christopher R. Tate
*Assistant Examiner* — Deborah A. Davis
(74) *Attorney, Agent, or Firm* — Rick Matos; Innovar, L.L.C.

(57) ABSTRACT

A supercritical fluid (SCF) extract of a cardiac glycoside-containing plant mass is provided. The extract can be included in a pharmaceutical composition containing an extract-solubilizing amount of solubilizer. Oleandrin is included within the extract when a cardiac glycoside-containing plant, such as *Nerium oleander*, is extracted by SCF extraction. The extract can also contain one or more other SCF extractable pharmacologically active agents. The composition can be used to treat a wide range of disorders that are therapeutically responsive to a cardiac glycoside.

30 Claims, 7 Drawing Sheets

The effect of supercritical CO2 oleander extract on the growth of PANC-1 cells

**Anti-proliferative effect of hot water and supercritical $CO_2$ extracts of *Nerium oleander* in human melanoma BRO cells**

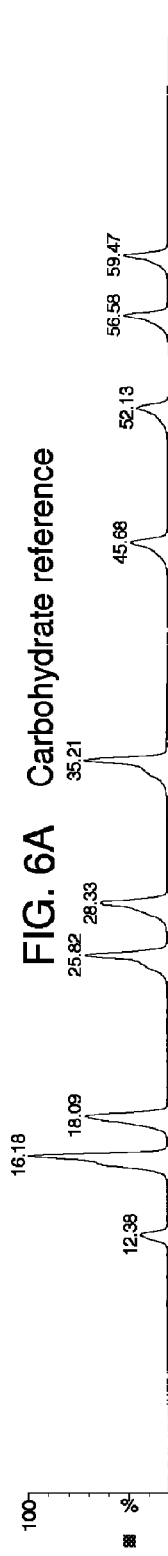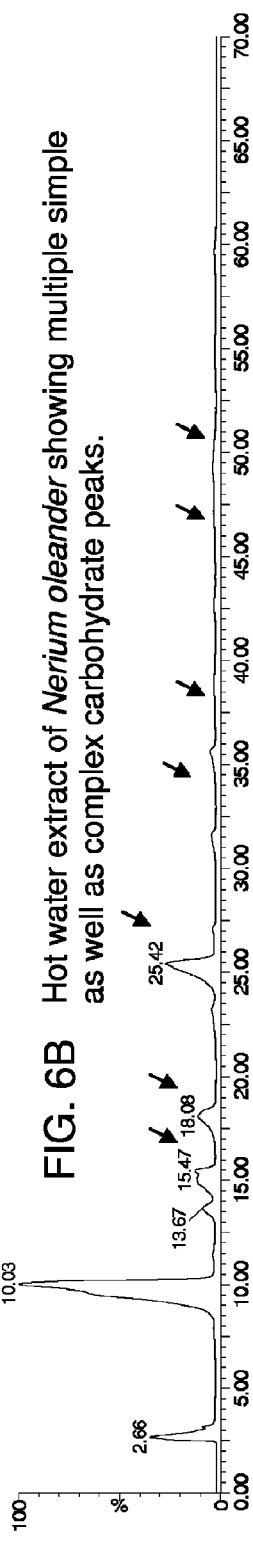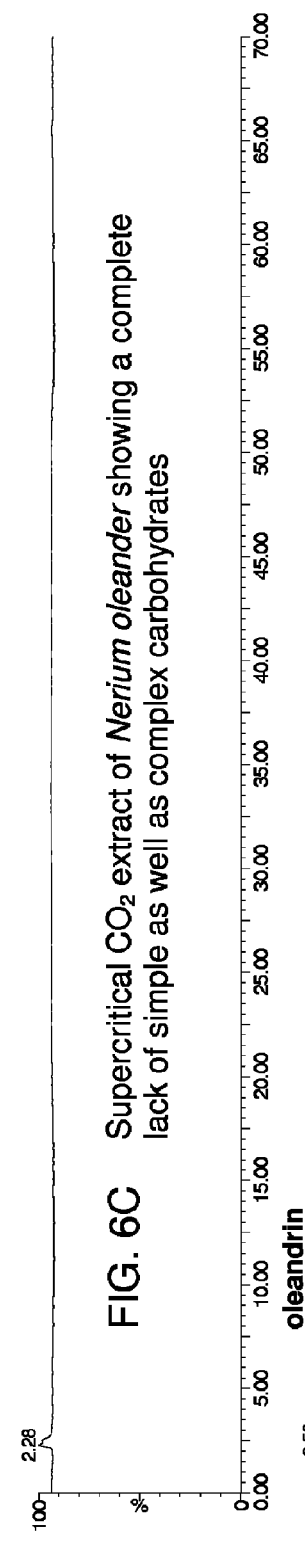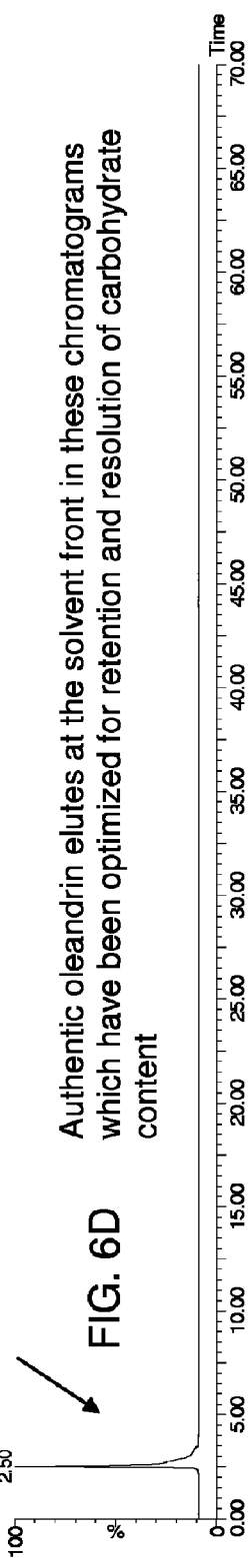

FIG. 6A Carbohydrate reference

FIG. 6B Hot water extract of *Nerium oleander* showing multiple simple as well as complex carbohydrate peaks.

FIG. 6C Supercritical $CO_2$ extract of *Nerium oleander* showing a complete lack of simple as well as complex carbohydrates FIG. 6D Authentic oleandrin elutes at the solvent front in these chromatograms which have been optimized for retention and resolution of carbohydrate content

SCF EXTRACT CONTAINING CARDIAC GLYCOSIDE

CROSS-REFERENCE TO EARLIER FILED APPLICATIONS

This application claims the benefit of and is a division of U.S. Ser. No. 12/019,435, filed Jan. 24, 2008, which is a continuation in part of PCT International Application No. PCT/US06/29061 filed Jul. 26, 2006, which claims the benefit of and is a continuation in part of U.S. application Ser. No. 11/191,650 filed Jul. 28, 2005, the entire disclosures of which are hereby incorporated by reference.

FIELD OF THE INVENTION

The present invention concerns a pharmaceutical formulation comprising oleandrin present as a supercritical fluid (SCF) extract comprising a cardiac glycoside. The formulation comprises one or more solubilizers, such as surfactants, that aid in solubilization, dispersion or emulsification of at least the cardiac glycoside, and optionally other pharmacologically active components of the extract, in the formulation when the formulation is placed in an aqueous environment. The invention also concerns SCF extracts comprising cardiac glycoside and methods of use thereof for the treatment of cardiac glycoside-responsive diseases or disorders.

BACKGROUND OF THE INVENTION

*Nerium oleander* is an ornamental plant widely distributed in subtropical Asia, the southwestern United States, and the Mediterranean. Its medical and toxicological properties have long been recognized. It has been used, for example, in the treatment of hemorrhoids, ulcers, leprosy, snake bites, and even in the induction of abortion. Oleandrin, an important component of oleander extract, is a potent inhibitor of human tumor cell growth (Afaq F et al. *Toxicol. Appl. Pharmacol.* 195:361-369, 2004). Oleandrin-mediated cell death is associated with calcium influx, release of cytochrome C from mitochondria, proteolytic processes of caspases 8 and 3, poly (ADP-ribose) polymerase cleavage, and DNA fragmentation.

It has been demonstrated that oleandrin is the principal cytotoxic component of *Nerium oleander* (Newman, et al., *J. Herbal Pharmacotherapy*, vol. 13, pp. 1-15, 2001). Oleandrin is a cardiac glycoside that is exogeneous and not normally present in the body. Oleandrin induces apoptosis in human but not in murine tumor cell lines (Pathak et al., *Anti-Cancer Drugs*, vol. 11, pp. 455-463, 2000), inhibits activation of NF-kB (Manna et al., *Cancer Res.*, vol. 60, pp. 3838-3847, 2000), and mediates cell death in part through a calcium-mediated release of cytochrome C (McConkey et al., *Cancer Res.*, vol. 60, pp. 3807-3812, 2000). A Phase I trial of a hot water oleander extract has been completed recently (Mekhail et al., *Am. Soc. Clin. Oncol.*, vol. 20, p. 82b, 2001). It was concluded that oleander extracts can be safely administered at doses up to 1.2 ml/m$^2$/d. No dose limiting toxicities were found.

In addition to being selectively cytotoxic for tumor cells, cardiac glycosides may also enhance cell response to cytotoxic actions of ionizing radiation. Ouabain, a cardiac glycoside endogeneous to the body, was reported to enhance in vitro radiosensitivity of A549 human lung adenocarcinoma cells but was ineffective in modifying the radioresponse of normal human lung fibroblasts (Lawrence, *Int. J. Radiat. Oncol. Biol. Phys.*, vol. 15, pp. 953-958, 1988). Ouabain was subsequently shown to radiosensitize human tumor cells of different histology types including squamous cell carcinoma and melanoma (Verheye-Dua et al., *Strahlenther. Onkol.*, vol. 176, pp. 186-191, 2000). Although the mechanisms of ouabain-induced radiosensitization are still not fully explained, inhibition of repair from sublethal radiation damage and an increase in radiation-induced apoptosis have been advanced as possibilities (Lawrence, 2000; Verheye Dua et al., 2000; Verheye-Dua et al., *Strahlenther. Onkol.*, vol. 172, pp. 156-161, 1996). The cardiac glycoside oleandrin also has the ability to enhance the sensitivity of cells to the cytotoxic action of ionizing radiation. See U.S. patent application Ser. No. 10/957,875 to Newman, et al. and Nasu et al., *Cancer Lett.* Vol 185, pp. 145-151, 2002).

Chen et al. (*Breast Cancer Research and Treatment* (2006), 96, 1-15) suggest that cardiac glycosides, such as ouabain and digitalis, might be useful toward developing anti-breast cancer drugs as both Na$^+$, K$^+$-ATPase inhibitors and ER antagonists.

Smith et al. (*Biochemical Pharmacology* (2000), 62, 1-4) report that ANVIRZEL, and its key cardiac glycoside component oleandrin, inhibits the exportation of fibroblast growth factor-2 (FGF-2) from the prostate cancer cell lines PC3 and DU145.

Newman et al. (*J. Experimental Therapeutics and Oncology* (2006), 5, 167-181) report that incubation of human malignant melanoma BRO cells with oleandrin results in a time-dependent formation of reactive oxygen species, superoxide anion radicals, that mediate mitochondrial injury and loss of cellular GSH pools.

U.S. Pregrant Patent Application Publication No. 20050112059 to Newman et al. discloses the enhancement of radiotherapy in the treatment of cancer by administration of oleandrin.

Extraction of glycosides from plants of *Nerium* species has traditionally been carried out using boiling water. The process of using boiling water as an extraction method to obtain active ingredients from *Nerium oleander* yields many products. Among these are oleandrin, nerine, and other cardiac glycoside compounds. The plant extracts are useful in the treatment of cell-proliferative diseases in animals.

Oleandrin extracts obtained by hot-water extraction of *Nerium oleander*, sold under the trademark ANVIRZEL™, are commercially available and contain the concentrated form or powdered form of a hot-water extract of *Nerium oleander*. The extract is prepared according to the process developed by Dr. Huseyin Ziya Ozel. U.S. Pat. No. 5,135,745 describes a procedure for the preparation of the extract of the plant in water. The extraction of the plant *Nerium oleander* involves slicing the leaves, cooking the sliced leaves and stems of the plant in water for 2-3 hours and filtering off the residues. The mixture is heated again. The aqueous extract reportedly contains several polysaccharides with molecular weights varying from 2 KD to 30 KD, oleandrin and oleandrigenin, odoroside and neritaloside. The polysaccharides reportedly include acidic homopolygalacturonans or arabinogalaturonans. Ozel (ibid, and *Planta Med.* 56 (1990), 668) incorrectly reports that the cardiac glycosides are not responsible for the antitumor activity of the aqueous extract.

Muller et al. (*Pharmazie.* (1991) September 46(9), 657-663) disclose the results regarding the analysis of a water extract of *Nerium oleander*. They report that the polysaccharide present is primarily galacturonic acid. Other saccharides include rhamnose, arabinose and galactose. Polysaccharide content and individual sugar composition of polysaccharides within the hot water extract of *Nerium oleander* have also been reported by Newman et al. (*J. Herbal Pharmacotherapy*, (2001) vol 1, pp. 1-16).

U.S. Pat. No. 5,869,060 to Selvaraj et al. pertains to extracts of *Nerium* species and methods of production. To prepare the extract, plant material is placed in water and boiled. The crude extract is then separated from the plant matter and sterilized by filtration. The resultant extract can then be lyophilized to produce a powder.

U.S. Pat. No. 6,565,897 (U.S. Pregrant Publication No. 20020114852 and PCT International Publication No. WO 2000/016793 to Selvaraj et al.) discloses a hot-water extraction process for the preparation of a substantially sterile extract.

Erdemoglu et al. (*J. Ethnopharmacol.* (2003) November 89(1), 123-129) discloses results for the comparison of aqueous and ethanolic extracts of plants, including *Nerium oleander*, based upon their anti-nociceptive and anti-inflammatory activities.

Organic solvent extracts of *Nerium oleander* are also disclosed by Adome et al. (*Afr. Health Sci.* (2003) August 3(2), 77-86; ethanolic extract), el-Shazly et al. (*J. Egypt Soc. Parasitol.* (1996), August 26(2), 461-473; ethanolic extract), Begum et al. (*Phytochemistry* (1999) February 50(3), 435-438; methanolic extract), Zia et al. (*J. Ethnolpharmacol.* (1995) November 49(1), 33-39; methanolic extract), and Vlasenko et al. (*Farmatsiia.* (1972) September-October 21(5), 46-47; alcoholic extract).

Supercritical fluid extraction involves the use of a supercritical fluid to selectively extract a particular compound. A supercritical fluid is a liquid or a gas at atmospheric conditions, but becomes supercritical when it is compressed above its critical pressure and heated above its critical temperature. Supercritical fluids have increased dissolving power in their supercritical regions. A supercritical fluid exhibits properties between those of a gas and a liquid, and has the capacity to dissolve compounds that may only dissolve poorly or not at all in the gas or liquid state. Supercritical fluids are ideal for extraction of these compounds because they have high dissolving power at high densities and demonstrate good fractionation and separation of the compound from the fluid at lower densities when the pressure or temperature is changed. The general procedure of using supercritical carbon dioxide extraction in food processing industry has been described by Raventos, et al., in 2002 (M. Raventos, et al., Application and Possibilities of Supercritical $CO_2$ Extraction in Food Processing Industry: An Overview, *Food Sci. Tech. Int.* Vol. 8 (5) (2002) 269-284), the entire content of which is hereby incorporated by reference. Raventos et al. report that SCF extraction is not suitable for extraction of polysaccharides from plant material even though he suggests that a modifier such as ethanol may be used to modify the performance of an SCF extraction.

U.S. Pregrant Patent Application Publication No. 20040247660 to Singh et al. discloses the preparation of a protein stabilized liposomal formulation of oleandrin for use in the treatment of cancer.

U.S. Pregrant Patent Application Publication No. 20050026849 to Singh et al. discloses a water soluble formulation of oleandrin containing a cyclodextrin. The '849 Publication suggests the preparation of solid-filled capsules containing the cyclodextrin complex of oleandrin. The oleandrin has been provided as the hot-water extract or the chemical entity and then treated with the cyclodextrin to form the complex.

U.S. Pregrant Patent Application Publication No. 20040082521 to Singh et al. discloses the preparation of protein stabilized nanoparticle formulations of oleandrin from the hot-water extract. The nanoparticles are prepared via formation of a liposomal mixture and subsequent evaporation of the organic solvent therein.

Methods to enhance the relative content of oleandrin from plant material are therefore warranted. While hot water extracts of *Nerium oleander* may provide oleandrin and related cardiac glycosides in relatively low yield, an improved method for obtaining a concentrated form of cardiac glycosides including oleandrin is needed.

Oleandrin contains a lactone ring that is acid labile and predisposes the material to acid degradation when orally dosed, so care must be taken in the preparation of liquid formulations to ensure minimization of acidic species in solution.

None of the known art discloses a pharmaceutical formulation comprising an extract of *Nerium* species, in particular, *Nerium oleander*. None of the art discloses or suggests a supercritical fluid extract comprising a cardiac glycoside, such as oleandrin. A need remains for more dosage forms that provide suitable delivery of the components of an extract of *Nerium* species for the treatment of various diseases and disorders. A need also remains for improved processes for obtaining cardiac glycosides by extraction from plant material.

SUMMARY OF THE INVENTION

The present invention seeks to overcome some or all of the disadvantages inherent in the art. The invention provides a supercritical fluid (SCF) extract comprising cardiac glycoside. The extract can be obtained by supercritical fluid extraction of a cardiac glycoside-containing plant mass. The plant mass can be *Nerium* species or *Thevetia* species plant mass. Particular species include *Nerium oleander* or *Thevetia nerifolia*. The supercritical fluid extract can comprise at least one other pharmacologically active agent that contributes to the therapeutic efficacy of the cardiac glycoside when the extract is administered to a subject. It can contribute additively or synergistically to therapeutic efficacy.

The invention also provides a pharmaceutical composition comprising a SCF extract comprising a cardiac glycoside. The cardiac glycoside can be present as the primary therapeutic component in the pharmaceutical composition, and one or more other therapeutic components may also be present. Some embodiments of the invention include an extract of oleander plant, such as of *Nerium* species, e.g. *Nerium oleander*, or such as of or of *Thevetia* species, e.g. *Thevetia nerifolia*. The extract can be prepared by supercritical fluid (SCF) carbon dioxide ($CO_2$) extraction of plant material, such as a dried powder of plant mass, by a process described herein or in a currently-pending U.S. application Ser. No. 60/653,210 filed Jul. 28, 2005 in the name of C. Addington and U.S. application Ser. No. 11/191,650 filed Jul. 28, 2005 in the name of C. Addington, the entire disclosures of which are hereby incorporated by reference, or by a process described herein. The SCF extraction can be conducted in the presence of a modifier to enhance extraction of the desired compound(s) from the plant mass.

Accordingly, the invention also provides a supercritical fluid extraction process of a cardiac glycoside-containing plant mass. The process comprises:

treating a cardiac glycoside-containing plant mass with a supercritical fluid for a period of time sufficient to extract the cardiac glycoside from the plant mass;

separating the plant mass from the supercritical fluid; and removing the supercritical fluid thereby forming a supercritical fluid (SCF) extract comprising cardiac glycoside.

The supercritical fluid can further comprise a modifier. The cardiac glycoside can be present as the primary therapeutic component in the extract, and the SCF extract can further comprise at least one other pharmacologically active agent aside from the cardiac glycoside. The other active agent may contribute to the therapeutic efficacy of the cardiac glycoside when the extract is administered to a subject. The other active agent may function additively or synergistically to contribute to the therapeutic efficacy of the cardiac glycoside. The cardiac glycoside-containing plant mass can comprise *Nerium* species or *Thevetia* species. In some embodiments, the other therapeutic agent is not a polysaccharide, such as an acidic homopolygalacturonan or arabinogalaturonan. In some embodiments, the extract excludes another therapeutic agent and/or excludes an acidic homopolygalacturonan or arabinogalaturonan. In some embodiments, the extract comprises one or more cardiac glycosides and one or more cardiac glycoside precursors (such as cardenolides, cardadienolides and cardatrienolides, all of which are the aglycone constituents of cardiac glycosides, for example, digitoxin, acetyl digitoxins, digitoxigenin, digoxin, acetyl digoxins, digoxigenin, medigoxin, strophanthins, cymarine, ouabain, or strophanthidin). The extract may further comprise one or more glycone constituents of cardiac glycosides (such as glucoside, fructoside, and/or glucuronide) as cardiac glycoside presursors. Accordingly, the extract may comprise one or more cardiac glycosides and two more cardiac glycoside precursors selected from the group consisting of one or more aglycone constituents, and one or more glycone constituents. An advantage of the composition, and dosage form thereof, of the invention is its ability to provide a solution of the entire, or of at least a major portion of, extract following oral administration such that all of the components are solubilized, emulsified or dispersed when placed in an aqueous environment. Solubilization, dispersion or emulsification can be the result of simple dissolution, micelle formation or self-emulsification depending upon the combination of excipients used in the composition. In some embodiments, solubilization of the SCF extraction is not pH dependent. Another advantage is substantially complete dissolution of all of the extract components in a pharmaceutical liquid composition comprising the SCF extract.

In some embodiments, the formulation comprises a combination of at least two materials selected from the group consisting of a water soluble (miscible) co-solvent, a water insoluble (immiscible) co-solvent, a surfactant, an antioxidant, a chelating agent, an absorption enhancer and the SCF extract.

One aspect of the invention provides a pharmaceutical composition comprising:
 a supercritical fluid extract of oleander plant mass; and
 an extract-solubilizing amount of at least one solubilizer.

In some embodiments of the invention, the oleander plant mass comprises *Nerium* species, such as *Nerium oleander*, or of *Thevetia* species, such as *Thevetia nerifolia* (otherwise known as yellow oleander). The oleander plant mass is a cardiac glycoside-containing plant mass. The cardiac glycoside can be oleandrin.

Another aspect of the invention provides a capsule formulation comprising a capsule shell, and a pharmaceutical composition as described herein. In some embodiments, the capsule formulation comprises:
 a capsule shell;
 an oleandrin extract obtained by supercritical fluid extraction of *Nerium* species; and
 an extract-solubilizing amount of at least one solubilizer.

The capsule formulation can be a solid, liquid, or semi-solid. The solubilizer can comprise a single component or a mixture of two, three, four, five or more components. Such components may be selected from the group consisting of water soluble (miscible) co-solvent, water insoluble (immiscible) co-solvent, surfactant, and antioxidant.

Some embodiments of the invention comprise the SCF extract and:
 at least one water miscible solvent;
 at least one antioxidant; and
 at least one surfactant.

The solubilizer is at least a single surfactant, but it can also be a combination of materials such as a combination of: a) surfactant and water miscible solvent; b) surfactant and water immiscible solvent; c) surfactant, antioxidant; d) surfactant, antioxidant, and water miscible solvent; e) surfactant, antioxidant, and water immiscible solvent; f) surfactant, water miscible solvent, and water immiscible solvent; or g) surfactant, antioxidant, water miscible solvent, and water immiscible solvent.

The composition optionally further comprises: a) at least one liquid carrier; b) at least one emulsifying agent; c) at least one solubilizing agent; d) at least one dispersing agent; e) at least one other excipient; or f) a combination thereof.

In some embodiments, water miscible solvent is low molecular weight (less than 6000) PEG, glycol, or alcohol. In some embodiments, the surfactant is a pegylated surfactant, meaning a surfactant comprising a poly(ethylene glycol) functional group.

Prior to oral administration or exposure to an aqueous solution, some embodiments of the composition are clear, and others are suspensions. Some embodiments of the invention form an emulsion, micellar dispersion or solid dispersion (suspension) in the gastrointestinal (GI) tract of a subject after oral administration or in an aqueous medium.

The dosage form of the invention is adapted for oral administration to a subject and is suitable for the treatment of malignant neoplastic disease, cancer, tumor, viral infection and other indications, disorders or symptoms that are therapeutically responsive to a cardiac glycoside, such as oleandrin. As used herein, the term "subject" is taken to mean warm blooded animals such as mammals, for example, cats, dogs, mice, guinea pigs, horses, bovine cows, sheep, and humans. Examples 7-9 provide exemplary procedures for the treatment of various disorders with an SCF extract of the invention. Cancer of the rectum, anus, colorectal tissues, head and neck tissues, esophageal tissue, lung (both non small cell and small cell carcinomas), breast, stomach, pancreas, prostate, liver, kidney, bladder, ureter, ovarian tissue, carcinoid tumors, sarcomas of bone, mesothelioma, and neoplasms of the central nervous system can be treated with the SCF extract.

The extract, pharmaceutical composition and pharmaceutical dosage form of the invention can be used to treat a viral infection. The method for determining the relative antiviral activity of extracts and cardiac glycosides of the invention is detailed in Example 12. Accordingly, a subject suffering from a viral infection is treated with a therapeutically effective amount of the SCF extract of the invention thereby providing relief of symptoms associate with or amelioration or prevention (prophylaxis) of the viral infection. A particular viral infect is HIV infection.

Some embodiments of the liquid composition are anhydrous or have no water added thereto. The composition may contain endogenous water already present in one or more of the components of the composition. Alternatively, the composition contains water added as a separate component thereof.

The invention provides an extract comprising one or more cardiac glycosides, wherein the extract has been prepared by SCF extraction of cardiac glycoside-containing plant material. In some embodiments, the SCF is carbon dioxide. In some embodiments, the SCF further comprises a modifier (extraction modifier). In some embodiments, the SCF extract further comprises at least one non-cardiac glycoside SCF extractable pharmacologically active agent obtained by way of the supercritical fluid extraction. The non-cardiac glycoside active agent might not contribute to the therapeutic efficacy of the cardiac glycoside when the extract is administered to a subject in need thereof. Alternatively, at least one other non-cardiac glycoside supercritical fluid extractable pharmacologically active agent functions additively or synergistically to contribute to the therapeutic efficacy of the cardiac glycoside when the extract is administered to a subject.

The invention also provides a method of treating a disease or disorder therapeutically responsive to cardiac glycoside therapy in a subject in need thereof, the method comprising administering to the subject a therapeutically effective amount of a supercritical fluid extract comprising a cardiac glycoside. The invention also provides a method of inhibiting or reducing the extent of Akt phosphorylation in a cancer cell or method of enhancing the expression of pERK in a cancer cell, the method comprising treating the cell with an effective amount of supercritical fluid extract comprising a cardiac glycoside. The invention also provides a method of inhibiting the proliferation of cancer cells comprising treating the cancer cells with an effective of amount supercritical fluid extract comprising a cardiac glycoside. The methods can be practiced in vivo or in vitro.

BRIEF DESCRIPTION OF THE FIGURES

The following figures form part of the present description and describe exemplary embodiments of the claimed invention. The skilled artisan will, in light of these figures and the description herein, be able to practice the invention without undue experimentation.

FIGS. 6A-6D depict comparative HPLC chromatograms for the carbohydrate analysis of a carbohydrate reference (FIG. 6A), a hot water extract (FIG. 6B, of *Nerium oleander* showing multiple simple as well as complex carbohydrate peaks), a SCF $CO_2$ extract (FIG. 6C, of *Nerium oleander* showing a complete lack of simple as well as complex carbohydrates), and oleandrin (FIG. 6D, authentic oleandrin elutes at the solvent front in these chromatograms which have been optimized for retention and resolution of carbohydrate content).

DETAILED DESCRIPTION OF THE INVENTION

Figure 1A:
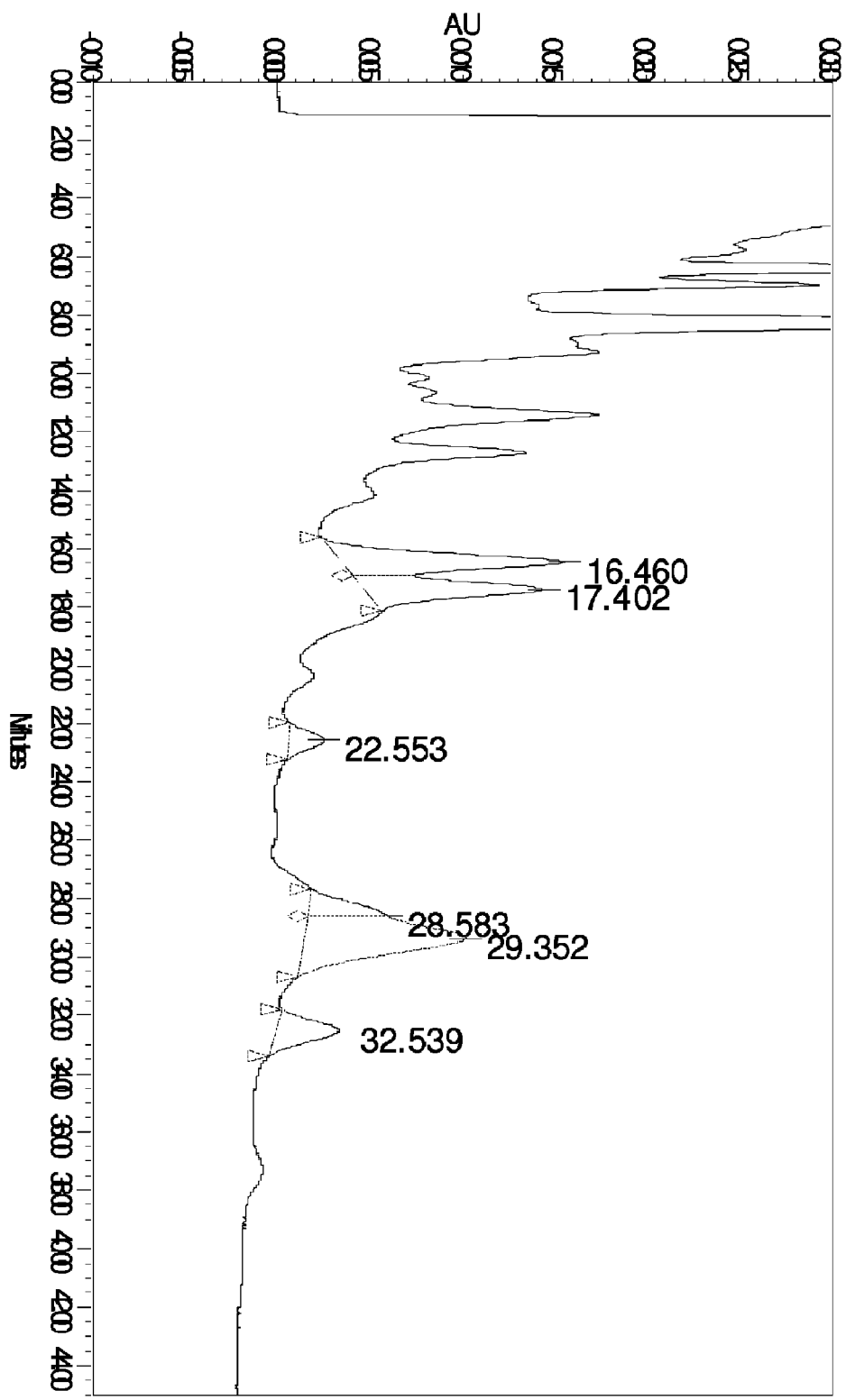
FIGS. 1A and 1B depict comparative HPLC chromatograms for a prior art hot-water extract and an exemplary supercritical fluid extract of the invention.

The extraction process can be conducted on a dried powder of *Nerium oleander* leaves prepared according to a process described in a currently-pending U.S. provisional application Ser. No. 60/653,210 filed Feb. 15, 2005 in the name of Addington or U.S. application Ser. No. 11/340,016 filed Jan. 26, 2006 in the name of Addington, the entire disclosures of which are hereby incorporated by reference.

An important component of the method for processing oleander leaves is the use of a patented comminuting and dehydrating system and method which utilizes vortexes of air to extract plant moisture and separate the plant particles by size. Suitable comminuting and dehydrating systems are described in U.S. Pat. No. 5,236,132, No. 5,598,979, No. 6,517,015, and No. 6,715,705, all to Frank Rowley, Jr., the entire disclosure of each of which is hereby incorporated by reference. In general, the method for processing oleander leaves involved collecting suitable leaves and stems, washing the collected plant material, drying the leaves and stems, and passing the leaves through an apparatus which uses vortexes of air to extract moisture and separate the plant particles by size. Larger particles were either re-processed or used as coarse material. The smallest particles were retained as fine oleander dust which can then be subjected to further extraction to obtain oleandrin and other pharmacologically active components.

Supercritical fluids are produced by heating a gas above its critical temperature or compressing a gas above its critical pressure. Supercritical fluid extraction comprises at least two steps: extraction and separation. An exemplary supercritical-fluid extractor comprises a tank of the mobile phase, usually $CO_2$, a pump to pressurize the gas, an oven containing the extraction vessel, a restrictor to maintain a high pressure in the extraction line, and a trapping vessel. Analytes are trapped by letting the solute-containing supercritical fluid decompress into an empty vial, through a solvent, or onto a solid sorbent material. Extractions are done in dynamic, static, or combination modes. In a dynamic extraction the supercritical fluid continuously flows through the sample in the extraction vessel and out the restrictor to the trapping vessel. In static mode the supercritical fluid circulates in a loop containing the extraction vessel for some period of time before being released through the restrictor to the trapping vessel. In the combination mode, a static extraction is performed for some period of time, followed by a dynamic extraction.

In general, the starting material is placed in an extractor device together with the supercritical fluid at specified pressure and temperature conditions to extract the desired components from the plant material. After extraction, the fluid and the compound are passed through a separator which changes the pressure and temperature, thereby reducing the dissolving power of the supercritical fluid and causing the separation or fractionation of the dissolved compound.

The SCF extract is prepared by mixing oleander plant starting material with carbon dioxide at a supercritical pressure and temperature, with or without a chemical modifier, then decreasing the pressure and temperature of the mixture and separating out the extract. The extract is separated as the pressure and temperature of the mixture are decreased. The use of powdered oleander leaves as a starting material is preferred. The powdered leaf particles ensure that a maximum amount of surface and internal leaf area is exposed to the extraction process. This provides an exponential increase in the amount of active components that are recovered in the extract, compared to methods of extraction currently available. The table below includes different solvents that can be used as the SCF extraction solvent and their corresponding critical temperature and critical pressure.

| Fluid | Critical Temperature (K) | Critical Pressure (bar) |
|---|---|---|
| Carbon dioxide | 304.1 | 73.8 |
| Ethane | 305.4 | 48.8 |
| Ethylene | 282.4 | 50.4 |
| Propane | 369.8 | 42.5 |
| Propylene | 364.9 | 46.0 |
| Trifluoromethane (Fluoroform) | 299.3 | 48.6 |
| Chlorotrifluoromethane | 302.0 | 38.7 |
| Trichlorofluoromethane | 471.2 | 44.1 |
| Ammonia | 405.5 | 113.5 |
| Water | 647.3 | 221.2 |
| Cyclohexane | 553.5 | 40.7 |
| n-Pentane | 469.7 | 33.7 |
| Toluene | 591.8 | 41.0 |

Carbon dioxide is a preferred supercritical fluid for the extraction of active components from the oleander plant. Its critical temperature is 31.06° C., its critical pressure is 73.83 bar, and its critical density is 0.460 g/cm$^3$. It is contemplated, however, that other compounds, or mixtures thereof, can be used in a SCF extraction process for oleandrin.

In some embodiments, a co-solvent or modifier is included in the supercritical fluid. Modifiers generally possess volatility between that of the supercritical fluid and of the compound being extracted, and they must be miscible with the supercritical fluid. In some embodiments, the modifier is a liquid at ambient conditions. By way of example and without limitation, a modifier can be selected from the group consisting of ethanol, methanol, propanol, water, acetone, ethyl acetate, methylene chloride, etc. (See table above). For the extraction of pharmacologically active components from the oleander plant, ethanol is a particularly suitable modifier. It can be used in a ratio of 35 to 75 kg ethanol solvent per kg of biomass although the preferred ratio is 55 kg solvent per kg biomass material. An exemplary extraction process for the SCF extraction of oleandrin from *Nerium oleander* can be conducted as follows or as detailed in Example 1. The starting comminuted plant material is combined with the carbon dioxide in an extractor device. Pure $CO_2$, or a mixture thereof with one or more modifiers, is employed as the supercritical solvent. The extraction is conducted at a pressure of about 280 bar or about 270 to 320 bar, and a temperature of about 50° C. or about 40 to 60° C. The ratio of solvent to raw starting material is preferably about 50:1 or about 45:1 to 60:1 based on weight of both the solvent and the raw material.

In another exemplary extraction process, supercritical carbon dioxide further comprising ethanol as a modifier is added to the starting plant material in an extractor device (see Example 1). The extraction is conducted at a pressure of about 280 bar (or about 270 to 320 bar), and a temperature of about 50° C. or about 40 to 60° C. The ratio of solvent and modifier to raw starting material is preferably from about 40 to about 45 to 1, based on the weight of both the solvent and modifier combined and the raw material. The ethanol modifier is subsequently evaporated by use of vacuum.

Following extraction, separation is conducted. In some exemplary embodiments, the supercritical solvent, with or without a modifier, in combination with the dissolved starting material, is passed through a separator device which decreases the pressure and temperature of the solvent mixture until the extract containing the active components is separated and recovered.

The extract is a mixture of pharmacologically active compounds, such as oleandrin or other cardiac glycosides, and other plant material. The oleandrin-rich extract obtained by the SCF process is a substantially water-insoluble, viscous semi-solid at ambient temperature. The SCF extract comprises many different components possessing a variety of different ranges of water solubility. Oleandrin extract from a supercritical fluid process contains by weight a theoretical range of 0.9% to 2.5% oleandrin. SCF extracts comprising varying amount of oleandrin have been obtained. In one embodiment, the SCF extract comprises about 2% by wt. of oleandrin. The remainder of the viscous semi-solid extract consists of water insoluble cellulose materials. The hot-water extract has different properties than and a different composition than the SCF extract. The SCF extract contains a 3-10 fold higher concentration of oleandrin than the hot-water extract. This was confirmed by both HPLC as well as LC/MS/MS (tandem mass spectrometry) analyses.

Figure 1B:
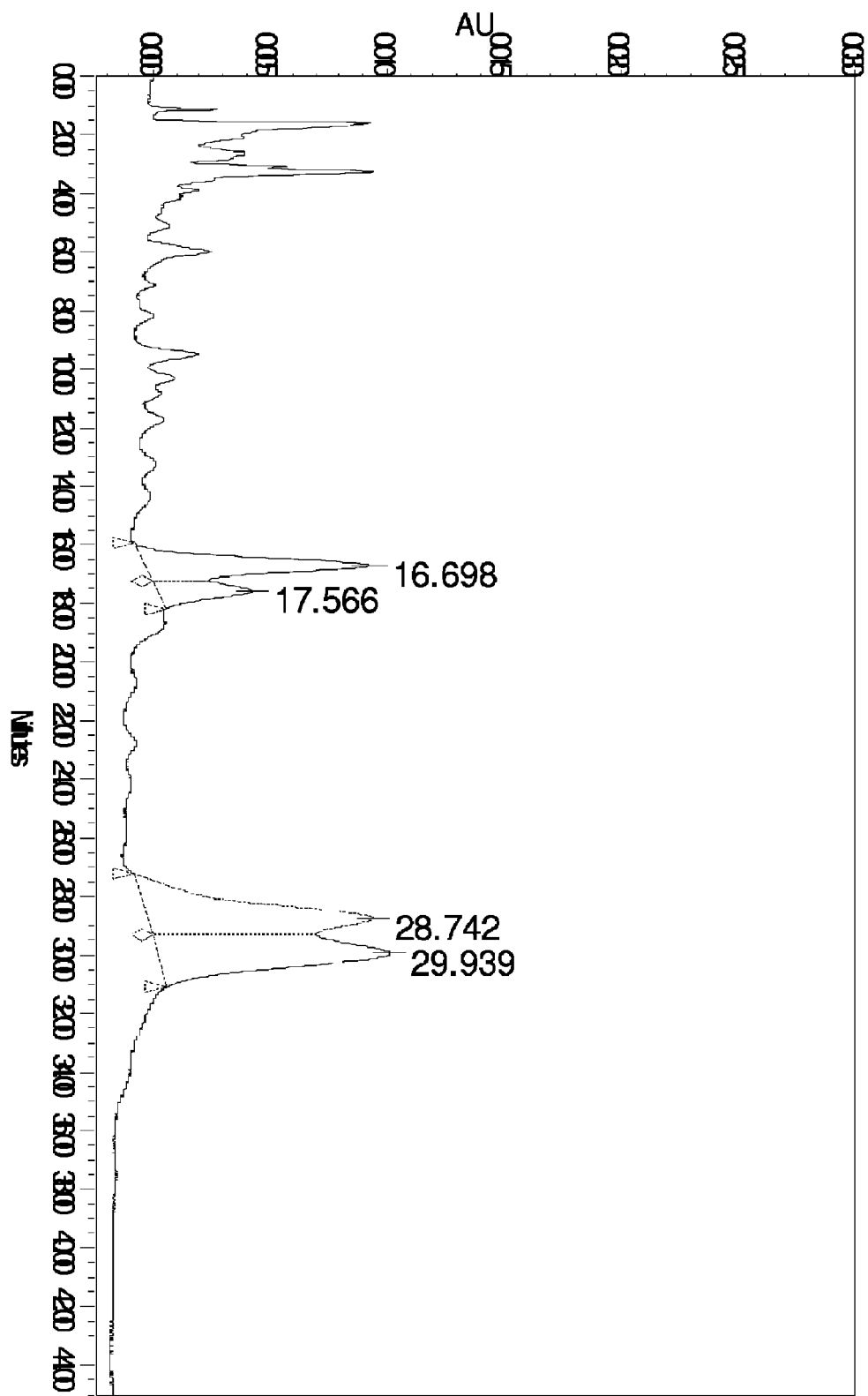

The hot-water extract of the prior art was compared to the SCF extract of the invention. FIG. 1A depicts an HPLC chromatogram for each the prior art hot water extract, and FIG. 1B depicts an HPLC chromatogram for each the SCF extract of the invention. The analysis was conducted as detailed in Example 11. The peak at 17.6 min is identified as oleaside A. The peak at 29.9 min is identified as oleandrin. The chromatograms were obtained by injecting samples of the extract at a concentration of 10 mg extract/ml of HPLC buffer. The data for the hot-water extract was obtained using a 30 μl injection volume and the data for the SCF extract was obtained using a 10 μl injection volume. The samples assayed as follows:

| Extract | Oleaside (%) | Oleandrin (%) |
|---|---|---|
| Hot-water | 0.094 | 0.17 |
| SCF | 0.73 | 2.68 |

The two extract differ substantially in their concentration of oleandrin, oleaside A and in the composition and relative amounts of their various other components that have not been identified herein. The concentration of oleandrin was increased by 15-fold due to the supercritical $CO_2$ extraction process. As a potential clinical treatment benefit, much smaller amount of supercritical $CO_2$ extract will be needed to achieve similar activity and efficacy compared to the hot water extract. As a result, the supercritical $CO_2$ extract is expected to provide maximal therapeutic efficacy and overcome the over-dosage drawback of hot water extract in order to achieve a similar therapeutic effect.

The extracts also differ in their polysaccharide and carbohydrate content. FIGS. 6A-6D depict HPLC chromatograms (with tandem MS detection) for a carbohydrate reference sample (mixture of simple saccharide and oligosaccharide standards ranging from a very simple sugar, d-xylose (molecular weight 150) to a relatively complex carbohydrate, maltoheptaose (molecular weight 1152)), a hot water extract, a SCF $CO_2$ extract, and oleandrin, respectively. The samples were analyzed according to Example 14. The reference sample includes a mixture of monosaccarides and disaccharides. The hot water extract contains 407.3 glucose equivalent units of carbohydrate relative to a standard curve prepared with glucose while analysis of the SCF $CO_2$ extract found carbohydrate levels that were found in very low levels that were below the limit of quantitation. The amount of carbohydrate in the hot water extract of Nerium oleander was, however, at least 100-fold greater than that in the SCF $CO_2$ extract. The polysaccharide content of the SCF extract can be <0.5%, <0.1%, <0.05%, or <0.01% wt.

| Nerium oleander preparation | Carbohydrate content (µg glucose equivalents/mg of plant extract) |
|---|---|
| Hot water extract | 407.3 ± 6.3 |
| SCF $CO_2$ extract | BLQ (below limit of quantitation) |

Based upon the findings above and LC/MS/MS data shown in FIG. 1, the SCF $CO_2$ extract contains no quantifiable sugar content in comparison to the hot water extract which is more than 40% carbohydrate by weight. It is extremely surprising that the SCF $CO_2$ extract, which contains no quantifiable amounts of polysaccharides in contrast to the hot water extract, actually exhibits by 15 to 20-fold more antiproliferative activity than the hot water extract.

Contrary to the teachings of Ozel (supra), the antiproliferative activity of the hot water extract is not attributable to polysaccharides therein. The polysaccharide components of the hot water extract were isolated by subjecting the hot water extract to passage through a small preparative C18 solid phase column. This type of column only removes non-water soluble (i.e. lipid soluble) components. As such, all water soluble carbohydrates whether as simple sugars or as complex polysaccharides simply pass through the column and are collected. The aqueous, solution containing the collected carbohydrates, was then brought to dryness under nitrogen. The dried carbohydrate material from the hot water extract of Nerium oleander was then reconstituted in water or tissue culture media and added to human melanoma cells to determine relative cytotoxic potential using an MTT assay that measures mitochondrial enzyme activity in live cells. This colorimetric microtiter based test therefore can be used to measure the relative ability of materials to inhibit proliferation of tumor cells. The relative antiproliferative activity of the polysaccharide components of the hot water extract (isolated by Ozel et al), the intact hot water extract and the total components of the instant SCF $CO_2$ extract were compared using this method.

Figure 7:
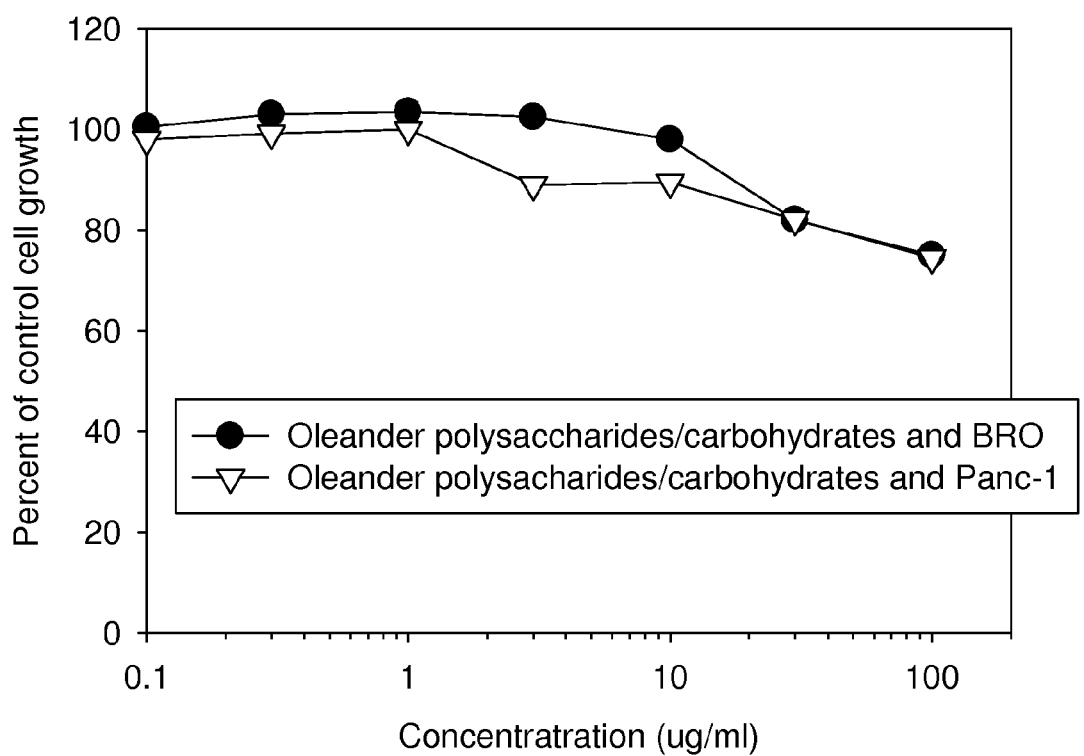
FIG. 7 is a semilog plot of concentration of oleandrin versus percent growth of control of human melanoma BRO and PANC-1 cells for polysaccharides isolated from the hot water extract. BRO or Panc-1 cells ($8\times10^3$)/well were plated in a 96 well plate and extracts were added in different concentrations. All stock solutions were made in saline and further dilutins were prepared in tissue culture media with 10% fetal calf serum. Cells were incubated with extracts for a period of 72 hours prior to determination of cell proliferation by MTT assay.

The data (see table below and FIG. 7) demonstrate that the components of the SCF $CO_2$ extract are extremely potent in inhibiting proliferation of human tumor cell lines and therefore should be efficacious in treating diseases associated with excessive cell proliferation; whereas, the polysaccharide components are not. In particular, once the cardiac glycosides (lipid soluble materials) are removed from the hot water extract of Nerium oleander, the extract is without any significant potential to inhibit the growth of malignant cells.

| Nerium oleander product or component | $IC_{50}$ (ug/ml)* Human BRO melanoma cancer cells | $IC_{50}$ (ug/ml) Human Panc-1 pancreatic cancer cells |
|---|---|---|
| Supercritical $CO_2$ extract (SCF $CO_2$) | 0.35 | 0.22 |
| Hot water extract | 6.1 | 3.3 |
| **Hot water extract without lipid (cardiac glycoside) components | >100 | >100 |

*The $IC_{50}$ value is that concentration of product which when incubated with cells in culture for a defined period of time (e.g. 72 hr) produces 50% inhibition of cell proliferation or survival.
**The removal of cardiac glycosides from the hot water extract leaves a product consisting almost entirely of simple as well as complex, that is linked, sugar resides. The later are also referred to as complex polysaccharides.

The partial compositions of the SCF $CO_2$ extract and hot water extract were determined by DART TOF-MS (Direct Analysis in Real Time Time of Flight Mass Spectrometry) on a JEOL AccuTOF-DART mass spectrometer (JEOL USA, Peabody, Mass., USA). The SCF extract was found to comprise some or all of the compounds selected from the group consisting of: oleandrin and oleandrigenin. The extract also comprised aglycone of odoroside and triterpenes (such as described in Phytochem. 1995, 39, 171-174, the entire disclosure of which is hereby incorporated by reference). Other compounds that might be present in the SCF extract include one or more of neritaloside; oleanolic acid; ursolic acid; betulinic acid; betulin (urs-12-ene-3β,28-diol); 28-norurs-12-en-3β-ol; urs-12-en-3β-ol; 3β,3β-hydroxy-12-oleanen-28-oic acid; 3β,20α-dihydroxyurs-21-en-38-oic acid; 3β,27-dihydroxy-12-ursen-38-oic acid; 3β,13β-dihydroxyurs-11-en-28-oic acid; 3β,12α-dihydroxyoleanan-28,13β-olide; 3β,27-dihydroxy-12-oleanan-28-oic acid; and other components. The hot water extract comprised high amounts of polysaccharide with only small amounts of oleandrin and oleandrigenin.

In some embodiments, the extract comprises one or more of the compounds listed in the table below or otherwise herein. The following table provides a brief summary of suitable plant material sources that are extractable with SCF and the cardiac glycosides derived therefrom, wherein the cardiac glycosides have demonstrated efficacy against the respectively listed cell lines. Accordingly, a SCF extract of the invention, or a pharmaceutical composition or dosage form comprising a SCF extract of the invention can also be used to treat the proliferative disorders included in the table below.

| Plant Species | Cardiac Glycoside(s) | Demstrated efficacy against |
|---|---|---|
| Apocynum cannabinum L. (Apocynaceae) | Apocannoside, cymarin | Human nasopharynx carcinoma (KB) |
| Asclepias curassavica L. (Asclepiadaceae) | Calotropin, 16α-acetoxycalotropin, 15β-hydroxycalotropin, calactin, 15β-hydroxycalactin, asclepin, 16α-hydroxyasclepin, uscharidin, uscharin, uzarigenin | Human lung carcinoma (A549), breast carcinomas (MCF-7 and MDA-MB-231), and hepatoma (HepG2) |

| Plant Species | Cardiac Glycoside(s) | Demstrated efficacy against |
|---|---|---|
| *Beaumontia brevituba* Oliver (Apocynaceae) | Digitoxigenin, oleandrigenin, digitoxigenin, α-L-cymaroside, digitoxigenin β-gentiobiosyl-α-L-cymaroside, $\Delta^{16}$-digitoxigenin β-D-glucosyl-α-L-cymaroside | Human breast carcinoma (BC1), colon carcinoma (Col2), fibrosarcoma (HT-1080), nasopharyngeal carcinoma (KB), vinblastine-resistant KB (KB-V1), lung carcinoma (Lu1), and melanoma (Mel2) |
| *Calotropis procera* (Ait.) R. Br. (Asclepiadaceae) | Calotropin, calactin, uscharin, voruscharin, 2″-oxovoruscharin | Human non-small-cell lung carcinoma (A549), human glioblastomas (Hs683 and U373), human colon carcinomas (HCT-15 and LoVo), hepatoma (Huh7), non-hepatoma (COS-1), and colorectal carcinoma (COLO 320) |
| *Cerbera odollam* Gaertner (Apocynaceae) | 2′-O-Acetyl cerleaside A, 17α-neriifolin, 17β-neriifolin, cerberin | Human oral epidermoid carcinoma (KB), breast carcinoma (BC), and small-cell lung carcinoma (NCI-H187) |
| *Coronilla varia* L. (Fabaceae) | Hyrcanoside | Human lymphocytic leukemia cells (P-388) and nasopharynx carcinomas (9KB) |
| *Crossopetalum gaumeri* (Loes.) Lundell (Celastraceae) | Securigenin-3β-O-β-6-deoxyguloside, 19-hydroxy-sarmentogenin-3β-O-β-6-deoxyguloside, sarmentogenin-3β-O-[α-allosyl-(1→4)-β-6-deoxyalloside], securigenin-3β-O-[α-allosyl-(1→4)-β-6-deoxyalloside] | Human oral epidermoid carcinoma (KB) |
| *Digitalis purpurea* L. (Scrophulariaceae) *Digitalis lanata* (Scrophulariaceae) | Digoxin, digitoxin, gitoxin | Human prostate carcinomas (LNCaP, DU145, PC3), renal adenocarcinoma (TK-10), breast adenocarcinoma (MCF-7), malignant melanoma (UACC-62), and chronic myelogenous leukemia (K-562) |
| *Elaeodendron* sp. | Elaeodendrosides | Human ovarian carcinoma (A2780) |
| *Euonymus alata* (Thunb.) Sieb. (Celastraceae) | Acovenosigenin A 3-O-α-L-ramnopyranoside, euonymoside A, euonymusoside A | Human oral epidermoid (KB), promyelocytic lymphoma (HL-60), non-small-cell lung carcinoma (A549), and cervix carcinoma (Hela) |
| *Euonymus sieboldianus* Blume (Celastraceae) | Euonymoside A | Human lung carcinoma (A549) and ovarian adenocarcinoma (SK-OV-3) |
| *Maquira calophylla* (P.&E.) C.C. Berg (Moraceae) | Maquiroside A | Human oral epidermoid carcinoma (KB) |
| *Nerium oleander* L. (Apocynaceae) | Oleander, oleandrin, cardenolide N-1, cardenolide N-4, 3β-O-(β-D-sarmentosyl)-16β-acetoxy-14-hydroxy-5β,14β-card-20-(22)-enolide, 16β-acetoxy-3β,14-dihydroxy-5β,14β-card-20-(22)-enolide | Human Jurkat leukaemia (T-cell), histiocytic lymphoma (U-937), promyelocytic lymphoma (HL-60), cervical carcinoma (Hela), breast carcinoma (MCF-7), prostate carcinomas (LNCap, DU145, PC3), malignant fibroblast (VA-13), and liver carcinoma (HepG2) |
| *Nierembergia aristata* D. Don (Solanaceae) | 17-epi-11α-hydroxy-6,7-dehydrostrophanthidin-3-O-β-boivinopyranoside; 6,7-dehydrostrophanthidin-3-O-β-boivinopyranoside; 6,7-dehydrostrophanthidin-3-O-β-oleandropyranoside | Human breast carcinoma (BC1), fibrosarcoma (HT), lung cancer (LU1), melanoma (Mel2), colon carcinoma (Col2), oral epidermoid (KB), drug resistant KB with and without vinblastine, |

-continued

| Plant Species | Cardiac Glycoside(s) | Demstrated efficacy against |
|---|---|---|
| | | epidermoid carcinoma (A-431), prostate carcinoma (LNCaP), hormone-dependent breast carcinoma (ZR-75-1), and glioma (U373) |
| *Ornithogalum umbellatum* L. (Hyacinthaceae) | Convallatoxin | Human oral epidermoid carcinoma (KB) |
| *Pergularia tomentosa* L. (Asclepiadaceae) | 3'-O-β-D-glucopyranosylcalactin, 12-dehydroxyghalakinoside, 6'-dehydroxyghalakinoside, ghalakinoside, calactin | Kaposis' sarcoma (KS) |
| *Periploca graeca* L. (Asclepiadaceae) | Periplocin isomers | Human prostate carcinoma (PC-3) |
| *Rhodea japonica* (Thunb.) Roth. (Liliaceae) | Rhodexin A | Human leukemia (K562) |
| *Saussurea stella* Maxim. (Asteraceae) | 3-O-β-D-fucopyranosylstrophanthidin, 3-O-β-D-quinovopyranosylperiplogenin, 3-O-β-D-glucopyranosyl-(1→4)-α-L-rhamnopyranosylcannogenin, 3-O-β-D-xylopyranosylperiplogenin, 3-O-β-D-quinovopyranosylstrophanthidin, 3-O-β-D-xylopyranosylstrophanthidin, 3-O-β-D-fucopyranosylperiplogenin, 3-O-α-L-rhamnopyranosylcannogenol, convallatoxin, 3-O-α-L-rhamnpyranosylacovenosigenin A | Human gastric cancer (BGC-823) and hepatoma (Bel-7402) |
| *Streblus asper* Lour. (Moraceae) | Stebloside, mansonin | Oral human epidermoid carcinoma (KB) |
| *Streptocaulon juventas* (Lour.) Merr. (Asclepiadaceae) | Periplogenin digitoxoside, Periplocymarin, digitoxigenin 3-O-[O-β-D-glucopyranosyl-(1→6)-O-β-D-glucopyranosyl-(1→4)-β-D-digitoxopyranoside, echujin, corchorusoside C | Human fibrosarcoma (HT-1080) |
| *Streptocaulon griffithii* Hook.f. (Asclepiadaceae) | 3-O-(β-glucopyranosyl)acovenosigenin A | Human gastrointestinal cancer (HCG-27), lung carcinoma (A549), breast carcinoma (MCF-7), and cervical carcinoma (HeLa) |
| *Strophanthus* | Ouabain | Human prostate carcinomas (LNCaP, DU145, PC3) |
| *Thevetia ahouia* (L.) A. DC. (Apocynaceae) | Neriifolin, 3'-O-methylevomonoside, 2'acetylneriifolin | National Cancer Institute's human disease oriented 60-cell line tumor screening panel |
| *Thevetia peruviana* (Pers.) K. Schum. (Apocynaceae) | Thevetin A and B, thevetoside | Human hepatoma (SMMC-7721), gastric carcinoma (SGC-7901), and cervical carcinoma (HeLa) |
| *Urginea maritime* (L.) Baker (Liliaceae) | Proscillaridin A, scillaren A | Human breast carcinoma (MCF-7) |

A cardiac glycoside obtained by SCF extraction can be subsequently modified to form an extract or composition comprising a semisynthetic cardiac glycoside. For example, a cardiac glycoside (oxovoruscharin, UNBS-1244) originally isolated from an African plant *Calotropis procera* can be modified to form semisynthetic UNBS-1450 (Mijatovic et al. *Drug Dev. Res.* (2007), 68(4), 164-173, and *Mol. Cancer. Ther.* (2006), 5(2), 391-399, the entire disclosures of which are hereby incorporated by reference).

Figure 4:
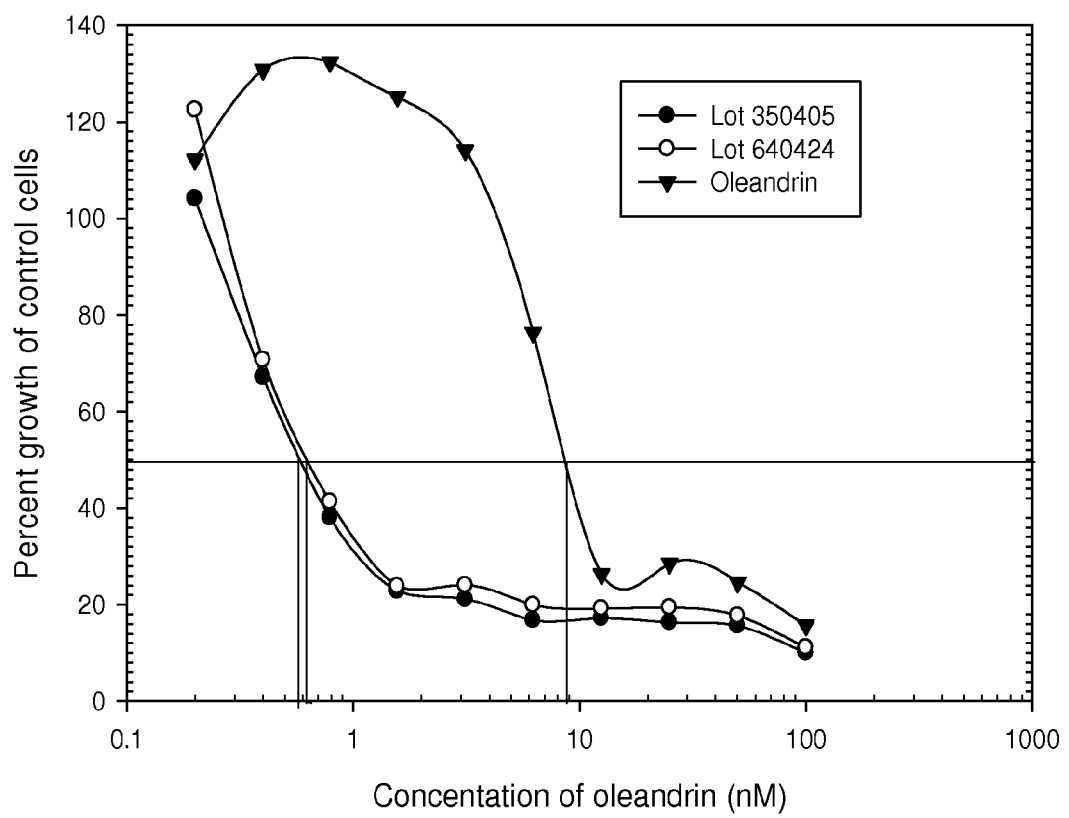
FIG. 4 is a plot of concentration of oleandrin versus percent growth of control of PANC-1 cells for two SCF extracts of the invention as compared to pure oleadrin.
Figure 5:
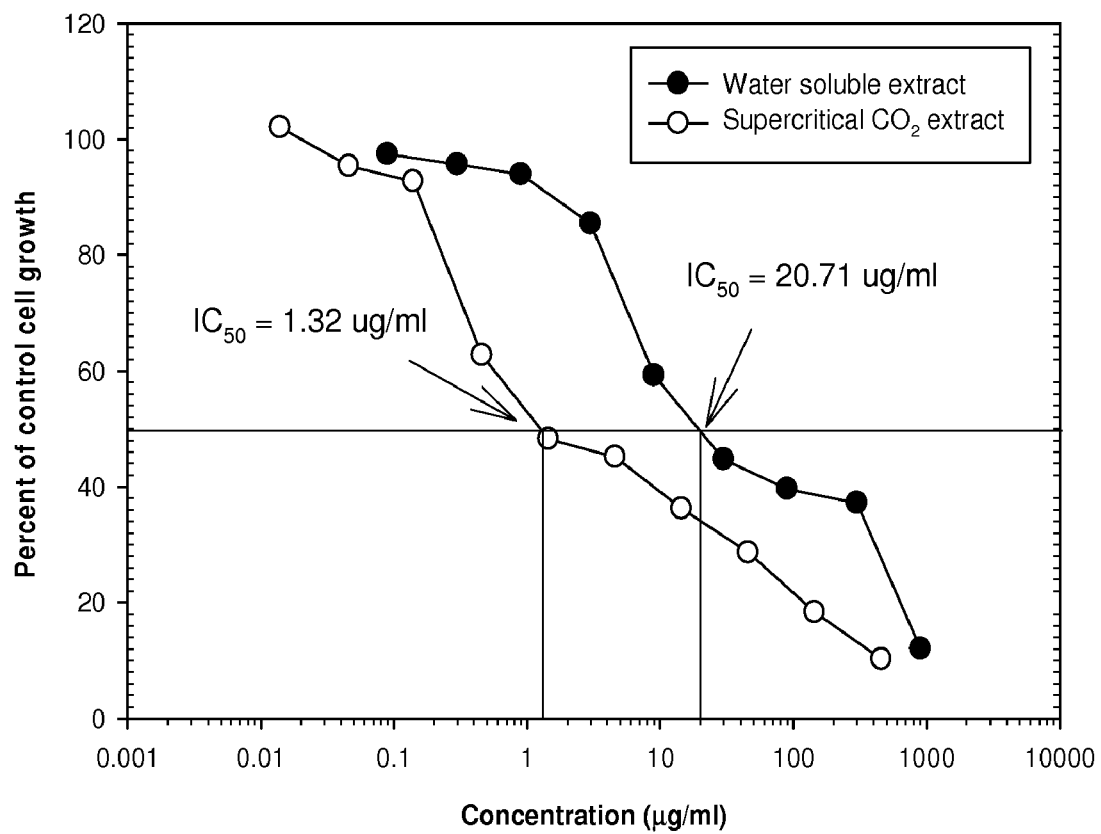
FIG. 5 is a semi-log plot of concentration of oleandrin versus percent growth of control of human melanoma BRO cells for an SCF extract of the invention as compared to a hot water extract.

The extracts also differ in their relative performance as determined by efficacy against several tumor cell lines (Example 10). Oleandrin-containing samples were prepared to contain the same amount of oleandrin although the concentration of oleandrin in each sample varied due to the differences in the concentration of in the extracts. The data obtained are summarized in the table below and in FIGS. 4 and 5.

| DRUG | Human melanoma BRO cells ($IC_{50}$, μM) | Human pancreatic cancer PANC-1 cells ($IC_{50}$, μM) |
|---|---|---|
| Oleandrin | 0.017* | 0.01 |
| Hot water extract | 0.052 | 0.03 |
| Supercritical $CO_2$ extract | 0.007 | 0.004 |

*The $IC_{50}$ of tested compounds are presented as micromolar (μM) oleandrin concentration in those extracts. That is, the data represent that concentration of oleandrin as free chemical or as part of an extract necessary to inhibit growth or proliferation of tumor cell growth compared to untreated cells by 50%.

As shown in the table above, the $IC_{50}$ value of the supercritical $CO_2$ extract is only 50% of that oleandrin alone in both Panc-1 and BRO cells, which suggested that the supercritical $CO_2$ extract of oleander is at least two-fold stronger (more potent) than oleandrin alone with respect to the inhibition of the growth of Panc-1 or BRO cells. In comparison, hot water extract was the least potent among three entities tested. The data demonstrate potent cytotoxicity against human tumor cell lines by oleandrin as well as the extracts with the relative potency occurring as follows: supercritical $CO_2$ extract>oleandrin>hot water extract. These data imply that the cytotoxicity of the supercritical $CO_2$ extract is probably due to the presence of at least one other pharmacologically active component in the SCF extract in addition to oleandrin and that the potency of the supercritical $CO_2$ extract is much greater (7.4 fold) than that of the hot water extract. The data (FIGS. 4 and 5) clearly demonstrate the substantial improvement in efficacy of the SCF extract over the hot-water extract and even oleandrin alone. The improvement in efficacy exceeded the expected improvement that might have been obtained based solely upon the increased concentration of oleandrin in the SCF extract.

Figure 3:
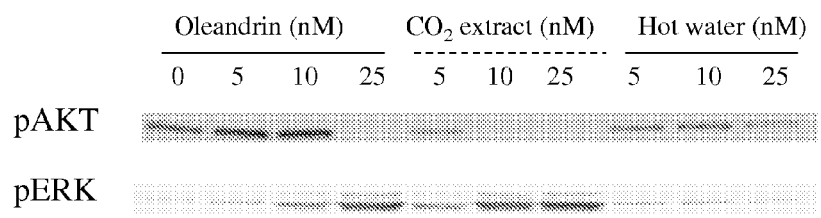
FIG. 3 depicts a photograph of the relevant bands of a gel electropherogram obtained as part of an assay comparing the activity of oleandrin, hot-water extract and the SCF extract of the invention toward inhibition of phosphoryation (active form) of Akt and augmentation of (phosphorylation) of Erk.

Phosphorylation of the serine/threonine kinase known as Akt provides tumor cells with enhanced survival capability. Increased Akt activity promotes survival of tumor cells that would normally undergo death by apoptosis. In addition, pAkt is involved in cell proliferation, angiogenesis, genome instability and cell invasion and migration (Yoeli-Lerner M and Toker A. Akt/PKB Signaling in Cancer. Cell Cycle 5:603-605, 2006). All of these responses contribute to initiation and progression. Further evidence of the importance of Akt signaling in cancer comes from studies which have detected over-expression and hyper-activation (through phosphorylation) of Akt in a wide range of human tumors, and this is often linked with poor prognosis. The relative activity of the hot-water and SCF extract on critical cell signaling proteins in human pancreatic cancer (Panc-1) cells were also compared. The data (FIG. 3) demonstrate a decreased activation (concentration-dependent decline in expression of the phosphorylated form pAkt) of protein kinase Akt and an increased activation of the MAPK/ERK (mitogen-activated protein kinase/extracellular signal-regulated kinase) pathway (concentration dependent increase in phosphorylated form pERK). Both oleandrin and supercritical $CO_2$ extract were capable of inhibiting PI3 Kinase resulting in reduction of phosphorylation of Akt in Panc-1 cells, whereas the hot water extract did not show this activity. Additionally, the expression of pERK was dramatically increased in cells treated with either oleandrin or supercritical $CO_2$ extract, but not in the cells treated with hot water extract. The relative ability of the supercritical $CO_2$ extract to inhibit pAkt expression is much greater than that of oleandrin or the hot water extract of *Nerium oleander*. Given the fact that phospho-Akt has been associated with cancer cell survival and increased drug and radiation resistance to cancer cells, inhibition of pAkt would lead to inhibition of proliferation of cancer cells. Therefore, these results suggest that supercritical $CO_2$ extract has a very similar mechanism of inhibition of proliferation of Panc-1 cells by suppressing the expression of pAkt and increasing the expression of pERK, but the effect is much stronger than that of oleandrin alone. We did not observe any similar changes in the cells treated with hot water extract. Accordingly, the invention provides a method of inhibiting or reducing the extent of Akt phosphorylation in a cancer cell by treating the cell with an effective amount of SCF extract of the invention. In some embodiments, the effective amount of extract is that amount equivalent to that containing an equivalent of at least 5 nM although a range of 5 to 50 nM is considered useful. Such a concentration of supercritical extract will be useful in terms of inhibiting tumor cell proliferation as well as tumor cell migration and metastases. In addition, inhibition of pAkt will prevent angiogenesis and, thus, tumor cell proliferation through inhibition of the development of blood and nutrient supply to the growing tumor.

The invention also provides a method of enhancing the expression of pERK (extracellular-signal-regulated kinase; ERK) in a cancer cell by treating the cell with an effective amount of SCF extract of the invention. In some embodiments, the effective amount of extract is at least 5 nM but a range of 5 nM to 50 nM is considered useful. Activation of ERK through phosphorylation is required for induction of autophagic tumor cell death and in addition leads to induction of p21, a protein involved in cell cycle arrest (inhibition of proliferation of tumor cells).

The invention also provides a method of inhibiting the proliferation of cancer cells by treatment of the cells with an effective of amount SCF extract of the invention.

The effect of oleandrin, the hot-water and SCF extract upon cell cycle changes of PANC-1 cells treated therewith was evaluated over a 24-hour period. Panc-1 cells were treated with 25 nM of oleandrin alone or the amount of hot water extract or supercritical $CO_2$ extract of oleander which was equivalent to 25 nM of oleandrin for 24 hrs. Cell cycle analysis was carried out by flow cytometry. Cell division consists of two consecutive processes, mainly characterized by DNA replication and then segregation of replicated chromosomes into two separate cells. Replication of DNA occurs in a specific part of the interphase called S phase. S phase is preceded by a gap called G1 during which the cell is preparing for DNA synthesis. This is 5 then followed by a gap called G2 during which the cell prepares for mitosis. Then this is followed with the mitosis phase, or M phase. G1, S, G2 and M phases are the traditional subdivisions of the standard cell cycle. Cells which are in a G2/M block such as that induced by the supercritical CO2 extract cannot undergo division. The data are summarized in the table below.

| Compounds | G1 phase | S phase | G2/M phase |
| --- | --- | --- | --- |
| Control | 37.0 | 47.7 | 15.4 |
| Oleandrin | 30.5 | 43.3 | 26.2 |
| Hot water extract | 33.0 | 38.8 | 23.2 |
| Supercritical $CO_2$ extract | 30.1 | 40.2 | 29.7 |

The data are expressed as the relative percentage of cells in a given phase of the cell cycle.

The data demonstrate that oleandrin as well as the other two oleander extracts all inhibit the proliferation of panc-1 cells through causing cells to arrest at the $G_2$/M phase. Again, the supercritical $CO_2$ extract at a similar concentration led to a stronger $G_2$/M phase arrest compared to oleandrin alone or hot water extract.

Based upon the data herein, the present inventors have demonstrated that the supercritical $CO_2$ extract can be specifically formulated to achieve a useful level of oral bioavailability. No such data is available for oral absorption of the prior art hot water extract.

As evidenced by the data herein, the SCF extract comprises a mixture of various components. Some of those components include oleandrin, oleaside A, oleandrigenin, neritaloside and odorside (Wang X, Plomley J B, Newman R A and Cisneros A. LC/MS/MS analyses of an oleander extract for cancer treatment. Alanytical Chem. 72: 3547-3552, 2000) and other unidentified components. The SCF extractable unidentified components of the SCF extract appear to include at least one other pharmacologically active component that contributes to the efficacy of the oleandrin in the SCF extract. The at least one other SCF extractable component functions additively or synergistically with the oleandrin to provide the observed efficacy.

Patients undergoing a therapeutic regimen with the hot water extract are required to self-administer a daily intramuscular bolus. Practitioners of the instant invention in a clinical setting could expect increased patient compliance with a treatment regimen when compared to that of an intramuscular route of administration. The practitioners could also expect increased acceptability (in terms of compliance) for the oral route of administration to subjects for long term therapy when compared to the daily intramuscular route of administration by intramuscular injection. The practitioners could also expect an improved ability to dose titrate the SCF extract as compared to a hot water extract since the hot water extract has limitations determined by the volume of the bolus. To the knowledge of the present inventors, no such limitations exist in the instant invention.

The formulation and pharmaceutical composition of the invention comprises an SCF extract of Nerium species and an extract-solubilizing amount of solubilizer. As used herein, the term "solubilizer" means a compound, or mixture of compounds, that aids in the dissolution, emulsification, or dispersion of one or more components, at least oleandrin, of the SCF extract in an aqueous environment. A solubilizer comprises one, two, three or more materials selected from the group consisting of a water soluble (miscible) co-solvent, a water insoluble (immiscible) co-solvent, an antioxidant, liquid carrier, surfactant and a combination thereof. Exemplary solubilizers include, by way of example and without limitation, those compounds disclosed in U.S. Pat. No. 6,451,339, the entire disclosure of which is hereby incorporated by reference. As used herein, the term "extract-solubilizing amount" refers to an amount of solubilizer sufficient to dissolve at least a substantial portion (at least 5% wt. or at least 25% wt. or at least 50% wt.) of the extract when the pharmaceutical composition is placed in an aqueous medium for a sufficient period of time, e.g. at least 10, at least 20 or at least 30 minutes. The solubilizer can comprise one, two, three, four, five or more excipients. The solubilizer can serve as a "solubilizing agent", meaning a compound, or mixture of compounds, that aids in dissolution of one or more components, at least oleandrin or another pharmacologically active agent, of the SCF extract in an aqueous environment. The solubilizer can also serve as an "emulsifying agent", meaning a compound, or mixture of compounds, that aids in emulsification of one or more components, at least oleandrin or another pharmacologically active agent, of the SCF extract in an aqueous environment.

It should be noted that a compound herein might possess one or more functions in the formulation of the invention. For example, a compound might serve as both a surfactant and a water miscible solvent or as both a surfactant and a water immiscible solvent.

Exemplary combinations of excipients in the solubilizer include at least the following: a) at least one water miscible solvent, at least one antioxidant, and at least one surfactant; b) at least one water miscible solvent and at least one surfactant; c) at least one water immiscible solvent, at least one water miscible solvent, at least one antioxidant, and at least one surfactant; and d) other combinations of two, three, four, five or more excipients.

Depending upon the combination of materials in the solubilizer, the liquid pharmaceutical composition can form a solution, micelle emulsion, dispersion, microparticulate or solid dispersion when placed in an aqueous environment, such as an assay solution or the GI tract of a subject following oral administration.

The liquid composition can comprise one or more pharmaceutically acceptable liquid carriers. The liquid carrier can be an aqueous, non-aqueous, polar, non-polar, and/or organic carrier. Liquid carriers include, by way of example and without limitation, a water miscible solvent, water immiscible solvent, water, buffer and mixtures thereof.

As used herein, the terms "water soluble solvent" or "water miscible solvent", which terms are used interchangeably, refer to an organic liquid which does not form a biphasic mixture with water or is sufficiently soluble in water to provide an aqueous solvent mixture containing at least five percent of solvent without separation of liquid phases. The solvent is suitable for administration to humans or animals. Exemplary water soluble solvents include, by way of example and without limitation, PEG (poly(ethylene glycol)), PEG 400 (poly(ethylene glycol having an approximate molecular weight of about 400), ethanol, acetone, alkanol, alcohol, ether, propylene glycol, glycerin, triacetin, poly(propylene glycol), PVP (poly(vinyl pyrrolidone)), dimethylsulfoxide, N,N-dimethylformamide, formamide, N,N-dimethylacetamide, pyridine, propanol, N-methylacetamide, butanol, soluphor (2-pyrrolidone), pharmasolve (N-methyl-2-pyrrolidone).

As used herein, the terms "water insoluble solvent" or "water immiscible solvent", which terms are used interchangeably, refer to an organic liquid which forms a biphasic mixture with water or provides a phase separation when the concentration of solvent in water exceeds five percent. The solvent is suitable for administration to humans or animals. Exemplary water insoluble solvents include, by way of example and without limitation, medium/long chain triglycerides, oil, castor oil, corn oil, vitamin E, vitamin E derivative, oleic acid, fatty acid, olive oil, softisan 645 (Diglyceryl Caprylate/Caprate/Stearate/Hydroxy stearate adipate), miglyol, captex (Captex 350: Glyceryl Tricaprylate/Caprate/Laurate triglyceride; Captex 355: Glyceryl Tricaprylate/Caprate triglyceride; Captex 355 EP/NF: Glyceryl Tricaprylate/Caprate medium chain triglyceride).

Suitable solvents are listed in the "International Conference on Harmonisation of Technical Requirements for Registration of Pharmaceuticals for Human Use (ICH) guidance for industry *Q3C Impurities: Residual Solvents*" (1997), which makes recommendations as to what amounts of residual solvents are considered safe in pharmaceuticals. Preferred solvents are listed as class 2 or class 3 solvents. Class 3 solvents include, for example, acetic acid, acetone, anisole, 1-butanol, 2-butanol, butyl acetate, tert-butlymethyl ether, cumene, ethanol, ethyl ether, ethyl acetate, ethyl formate, formic acid, heptane, isobutyl acetate, isopropyl acetate, methyl acetate, methyl-1-butanol, methylethyl ketone, methylisobutyl ketone, 2-methyl-1-propanol, pentane, 1-pentanol, 1-propanol, 2-propanol, or propyl acetate.

Other materials that can be used as water immiscible solvents in the invention include: Captex 100: Propylene Glycol Dicaprate; Captex 200: Propylene Glycol Dicaprylate/Dicaprate; Captex 200 P: Propylene Glycol Dicaprylate/Dicaprate; Propylene Glycol Dicaprylocaprate; Captex 300: Glyceryl Tricaprylate/Caprate; Captex 300 EP/NF: Glyceryl Tricaprylate/Caprate Medium Chain Triglycerides; Captex 350: Glyceryl Tricaprylate/Caprate/Laurate; Captex 355: Glyceryl Tricaprylate/Caprate; Captex 355 EP/NF: Glyceryl Tricaprylate/Caprate Medium Chain Triglycerides; Captex 500: Triacetin; Captex 500 P: Triacetin (Pharmaceutical Grade); Captex 800: Propylene Glycol Di(2-Ethylhexanoate); Captex 810 D: Glyceryl Tricaprylate/Caprate/Linoleate; Captex 1000: Glyceryl Tricaprate; Captex CA: Medium Chain Triglycerides; Captex MCT-170: Medium Chain Triglycerides; Capmul GMO: Glyceryl Monooleate; Capmul GMO-50 EP/NF: Glyceryl Monooleate; Capmul MCM: Medium Chain Mono- & Diglycerides; Capmul MCM C8: Glyceryl Monocaprylate; Capmul MCM C10: Glyceryl Monocaprate; Capmul PG-8: Propylene Glycol Monocaprylate; Capmul PG-12: Propylene Glycol Monolaurate; Caprol 10G10O: Decaglycerol Decaoleate; Caprol 3GO: Triglycerol Monooleate; Caprol ET: Polygycerol Ester of Mixed Fatty Acids; Caprol MPGO: Hexaglycerol Dioleate; Caprol PGE 860: Decaglycerol Mono-, Dioleate.

As used herein, a "surfactant" refers to a compound that comprises polar or charged hydrophilic moieties as well as non-polar hydrophobic (lipophilic) moieties; i.e., a surfactant is amphiphilic. The term surfactant may refer to one or a mixture of compounds. A surfactant can be a solubilizing agent, an emulsifying agent or a dispersing agent.

An empirical parameter commonly used to characterize the relative hydrophilicity and hydrophobicity of non-ionic amphiphilic compounds is the hydrophilic-lipophilic balance ("HLB" value). Surfactants with lower HLB values are more hydrophobic, and have greater solubility in oils, while surfactants with higher HLB values are more hydrophilic, and have greater solubility in aqueous solutions. Using HLB values as a rough guide, hydrophilic surfactants are generally considered to be those compounds having an HLB value greater than about 10, as well as anionic, cationic, or zwitterionic compounds for which the HLB scale is not generally applicable. Similarly, hydrophobic surfactants are compounds having an HLB value less than about 10.

It should be appreciated that the HLB value of a surfactant is merely a rough guide generally used to enable formulation of industrial, pharmaceutical and cosmetic emulsions. For many important surfactants, including several polyethoxylated surfactants, it has been reported that HLB values can differ by as much as about 8 HLB units, depending upon the empirical method chosen to determine the HLB value (Schott, *J. Pharm. Sciences,* 79(1), 87-88 (1990)). Likewise, for certain polypropylene oxide containing block copolymers (PLURONIC surfactants, BASF Corp.), the HLB values may not accurately reflect the true physical chemical nature of the compounds. Finally, commercial surfactant products are generally not pure compounds, but are complex mixtures of compounds, and the HLB value reported for a particular compound may more accurately be characteristic of the commercial product of which the compound is a major component. Different commercial products having the same primary surfactant component can, and typically do, have different HLB values. In addition, a certain amount of lot-to-lot variability is expected even for a single commercial surfactant product. Keeping these inherent difficulties in mind, and using HLB values as a guide, one skilled in the art can readily identify surfactants having suitable hydrophilicity or hydrophobicity for use in the present invention, as described herein.

The hydrophilic surfactant can be any hydrophilic surfactant suitable for use in pharmaceutical compositions. Such surfactants can be anionic, cationic, zwitterionic or non-ionic, although non-ionic hydrophilic surfactants are presently preferred. As discussed above, these non-ionic hydrophilic surfactants will generally have HLB values greater than about 10. Mixtures of hydrophilic surfactants are also within the scope of the invention.

Similarly, the hydrophobic surfactant can be any hydrophobic surfactant suitable for use in pharmaceutical compositions. In general, suitable hydrophobic surfactants will have an HLB value less than about 10. Mixtures of hydrophobic surfactants are also within the scope of the invention.

The choice of specific hydrophobic and hydrophilic surfactants should be made keeping in mind the particular hydrophobic therapeutic agent to be used in the composition, and the range of polarity appropriate for the chosen therapeutic agent, as discussed in more detail below. With these general principles in mind, a very broad range of surfactants is suitable for use in the present invention. Such surfactants can be grouped into the following general chemical classes detailed in the Tables below. The HLB values given in the Tables below generally represent the HLB value as reported by the manufacturer of the corresponding commercial product. Incases where more than one commercial product is listed, the HLB value is the Tables is the value as reported for one of the commercial products, a rough average of the reported values, or a value that, in the judgment of the present inventors, is more reliable. It should be emphasized that the invention is not limited to the surfactants in the following Tables, which show representative, but not exclusive, lists of available surfactants.

1. Polyethoxylated Fatty Acids

Although polyethylene glycol (PEG) itself does not function as a surfactant, a variety of PEG-fatty acid esters have useful surfactant properties. Among the PEG-fatty acid monoesters, esters of lauric acid, oleic acid, and stearic acid are most useful. Among the surfactants of Table 1, preferred hydrophilic surfactants include PEG-8 laurate, PEG-8 oleate, PEG-8 stearate, PEG-9 oleate, PEG-10 laurate, PEG-10 oleate, PEG-12 laurate, PEG-12 oleate, PEG-15 oleate, PEG-20 laurate and PEG-20 oleate. Examples of polyethoxylated fatty acid monoester surfactants commercially available are shown in Table 1.

TABLE 1

PEG-Fatty Acid Monoester Surfactants

| Compound | Commercial Product (Supplier) | HLB |
|---|---|---|
| PEG 4-100 monolaurate | Crodet L series (Croda) | >9 |
| PEG 4-100 monooleate | Crodet O series (Croda) | >8 |
| PEG 4-100 monostearate | Crodet S series (Croda), Myrj Series (Atlas/ICI) | >6 |
| PEG 400 distearate | Cithrol 4DS series (Croda) | >10 |
| PEG 100, 200, 300 monoleaurate | Cithrol ML series (Croda) | >10 |
| PEG 100, 200, 300 monooleate | Cithrol MO series (Croda) | >10 |
| PEG 400 dioleate | Cithrol 4DO series (Croda) | >10 |
| PEG 400-1000 monostearate | Cithrol MSseries (Croda) | >10 |
| PEG-1 stearate | Nikkol MYS-1EX (Nikko), Coster K1 (Condea) | 2 |
| PEG-2 stearate | Nikkol MYS-2 (Nikko) | 4 |
| PEG-2 oleate | NIkkol MYO-2 (Nikko) | 4.5 |
| PEG-4 laurate | Mapeg 200 ML (PPG), Kessco PEG 200 ML (Stepan), LIPOPEG 2L (LIPO Chem.) | 9.3 |
| PEG-4 oleate | Mapeg 200 MO (PPG), KEssco PEG200 MO (Stepan) | 8.3 |
| PEG-4 stearate | Kessco PEG 200 MS (Stepan), Hodag 20 S (Calgene), Nikkol MYS-4 (Nikko) | 6.5 |
| PEG-5 stearate | Nikkol TMGS-5 (Nikko) | 9.5 |
| PEG-5 oleate | NIkkol TMGO-5 (Nikko) | 9.5 |

TABLE 1-continued

PEG-Fatty Acid Monoester Surfactants

| Compound | Commercial Product (Supplier) | HLB |
|---|---|---|
| PEG-6 oleate | Algon OL 60 (Auschem SpA), Kessco PEG 300 MO (Stepan), Nikkol MYO-6 (Nikko), Emulgante A6 (Condea) | 8.5 |
| PEG-7 oleate | Algon OL 70 (Auschem SpA) | 10.4 |
| PEG-6 laurate | Kessco PEG300 ML (Stepan) | 11.4 |
| PEG-7 laurate | Lauridac 7 (Condea) | 13 |
| PEG-6 sterate | Kessco PEG300 MS (Stepan) | 9.7 |
| PEG-8 laurate | Mapeg 400 ML (PPG), LIPOPEG 4DL (Lipo Chem.) | 13 |
| PEG-8 oleate | Mapeg 400 MO (PPG), Emulgante A8 (Condea) | 12 |
| PEG-8 stearate | Mapeg 400 MS (PPG), Myrj 45 | 12 |
| PEG-9 oleate | Emulgante A9 (Condea) | >10 |
| PEG-9 stearate | Cremophor S9 (BASF) | >10 |
| PEG-10 laurate | Nikkol MYL-10 (Nikko), Lauridac 10 (Croda) | 13 |
| PEG-10 oleate | NIkkol MYO-10 (Nikko) | 11 |
| PEG-10 stearate | NikkolMYS-10 (Nikko), Coster K100 (Condea) | 11 |
| PEG-12 laurate | Kessco PEG 600 ML (Stepan) | 15 |
| PEG-12 oleate | Kessco PEG 600 MO (Stepan) | 14 |
| PEG-12 ricinoleate | (CAS #9004-97-1) | >10 |
| PEG-12 stearate | Mapeg 600 MS (PPG), Kessco PEG 600 MS (Stepan) | 14 |
| PEG-15 stearate | MIkkol TMGS-15 (Nikko), Koster K15 (Condea) | 14 |
| PEG-15 oleate | Nikkol TMGO-15 (Nikko) | 15 |
| PEG-20 laurate | Kessco PEG 1000 ML (Stepan) | 17 |
| PEG-20 oleate | Kessco PEG 1000 MO (Stepan) | 15 |
| PEG-20 stearate | Mapeg 1000 MS (PPG), Kessco PEG 1000 MS (Stepan), Myrj 49 | 16 |
| PEG-25 stearate | Nikkol MYS-25 (Nikko) | 15 |
| PEG-32 laurate | Kessco PEG 1540 ML (Stepan) | 16 |
| PEG-32 oleate | Kessco PEG 1540 MO (Stepan) | 17 |
| PEG-32 stearate | Kessco PEG 1540 MS (Stepan) | 17 |
| PEG-30 stearate | Myrj 51 | >10 |
| PEG-40 laurate | Crodet L40 (Croda) | 17.9 |
| PEG-40 oleate | Crodet O40 (Croda) | 17.4 |
| PEG-40 stearate | Myrj 52, Emerest 2715 (Henkel, Nikkol MYS-40 (Nikko) | >10 |
| PEG-45 stearate | NIkkol MYS-45 (Nikko) | 18 |
| PEG-50 stearate | Myrj 53 | >10 |
| PEG-55 stearate | Nikkol MYS-55 (Nikko) | 18 |
| PEG-100 oleate | Crodet O-100 (Croda) | 18.8 |
| PEG-100 stearate | Myrj 59, Arlacel 165 (ICI) | 19 |
| PEG-200 oleate | Albunol 200 MO (Taiwan Surf.) | >10 |
| PEG-400 oleate | LACTOMUL (Henkel), Albunol 400 MO (Taiwan Surf.) | >10 |
| PEG-600 oleate | Albunol 600 MO (Taiwan Surf.) | >10 |

2. PEG-Fatty Acid Diesters

Polyethylene glycol fatty acid diesters are also suitable for use as surfactants in the compositions of the present invention. Among the surfactants in Table 2, preferred hydrophilic surfactants, include PEG-20 dilaurate, PEG-20 dioleate, PEG-20 distearate, PEG-32 dilaurate and PEG-32 dioleate. Representative PEG-fatty acid diesters are shown in Table 2.

TABLE 2

PEG-Fatty Acid Diester Surfactants

| Compound | Commercial Product (Supplier) | HLB |
|---|---|---|
| PEG-4 dilaurate | Mapeg 200 DL (PPG), Kessco PEG 200 DL (Stepan), LIPOPEG 2-DL (Lipo Chem.) | 7 |
| PEG-4 dioleate | Mapeg 200 DO (PPG) | 6 |
| PEG-4 distearate | Kessco 200 DS (Stepan) | 5 |
| PEG-6 dilaurate | Kessco PEG 300 DL (Stepan) | 9.8 |
| PEG-6 dioleate | Kessco PEG 300 DO (Stepan) | 7.2 |
| PEG-6 distearate | Kessco PEG 300 DS (Stepan) | 6.5 |

TABLE 2-continued

PEG-Fatty Acid Diester Surfactants

| Compound | Commercial Product (Supplier) | HLB |
|---|---|---|
| PEG-8 dilaurate | Mapeg 400 DL (PPG), Kessco PEG 400 DL (Stepan), LIPOPEG 4 DL (Lipo Chem.) | 11 |
| PEG-8 dioleate | Mapeg 400 DO (PPG), Kessco PEG 400 DO (Stepan), LIPOPEG 4 DO (Lipo Chem.) | 8.8 |
| PEG-8 distearate | Mapeg 400 DS (PPG), CDS 400 (Nikkol) | 11 |
| PEG-10 dipalmitate | Polyaldo 2PKFG | >10 |
| PEG-12 dilaurate | Kessco PEG 600 DL (Stepan) | 11.7 |
| PEG-12 distearate | Kessco PEG 600 DS (Stepan) | 10.7 |
| PEG-12 dioleate | Mapeg 600 DO (PPG), Kessco 600 DO (Stepan) | 10 |
| PEG-20 dilaurate | Kessco PEG 1000 DL (Stepan) | 15 |
| PEG-20 dioleate | Kessco PEG 1000 DO (Stepan) | 13 |
| PEG-20 distearate | Kessco PEG 1000 DS (Stepan) | 12 |
| PEG-32 dilaurate | Kessco PEG 1540 DL (Stepan) | 16 |
| PEG-32 dioleate | Kessco PEG 1540 DO (Stepan) | 15 |
| PEG-32 distearate | Kessco PEG 1540 DS (Stepan) | 15 |
| PEG-400 dioleate | Cithrol 4DO series (Croda) | >10 |
| PEG-400 disterate | Cithrol 4DS series (Croda) | >10 |

3. PEG-Fatty Acid Mono- and Di-Ester Mixtures

In general, mixtures of surfactants are also useful in the present invention, including mixtures of two or more commercial surfactant products. Several PEG-fatty acid esters are marketed commercially as mixtures or mono- and diesters. Representative surfactant mixtures are shown in Table 3.

TABLE 3

PEG-Fatty Acid Mono- and Diester Mixtures

| Compound | Commercial Product (Supplier) | HLB |
|---|---|---|
| PEG 4-150 mono, dilaurate | Kessco PEG 200-6000 mono, dilaurate (Stepan) | N/A |
| PEG 4-150 mono, dioleate | Kessco PEG 200-6000 mono, dioleate (Stepan) | N/A |
| PEG 4-150 mono, Distearate | Kessco PEG 200-6000 mono, distearate (Stepan) | N/A |

4. Polyethylene Glycol Glycerol Fatty Acid Esters

Suitable PEG glycerol fatty acid esters are shown in Table 4. Among the surfactants in the Table, preferred hydrophilic surfactants are PEG-20 glyceryl laurate, PEG-30 glyceryl laurate, PEG-40 glyceryl laurate, PEG-20 glyceryl oleate, and PEG-30 glyceryl oleate.

TABLE 4

PEG Glycerol Fatty Acid Esters

| Compound | Commercial Product (Supplier) | HLB |
|---|---|---|
| PEG-20 glyceryl laurate | Tagat L (Goldschmidt) | 16 |
| PEG-30 glyceryl laurate | Tagat L2 (Goldschmidt) | 16 |
| PEG-15 glyceryllaurate | Glycerox L series (Croda) | 15 |
| PEG-40 glyceryl stearate | Glycerox L series (Croda) | 15 |
| PEG-20 glyceryl stearate | Capmul EMG (ABITEC), Aldo MS-20 KFG (Lonza) | 13 |
| PEG-20 glyceryl oleate | Tagat O (Goldschmidt) | >10 |
| PEG-30 glyceryl oleate | Tagat O2 (Goldschmidt) | >10 |

5. Alcohol Oil Transesterification Products

A large number of surfactants of different degrees of hydrophobicity or hydrophilicity can be prepared by reaction of alcohols or polyalcohols with a variety of natural and/or hydrogenated oils. Most commonly, the oils used are castor oil or hydrogenated castor oil, or an edible vegetable oil such as corn oil, olive oil, peanut oil, palm kernel oil, apricot kernel oil, or almond oil. Preferred alcohols include glycerol, sorbitol, and pentaerythritol. Among these alcohol-oil transesterified surfactants, preferred hydrophilic surfactants are PEG-35 castor oil (Incrocas-35), PEG-40 hydrogenated castor oil (Cremophor RH 40), PEG-25 trioleate (TAGAT TO), PEG-60 corn glycerides (Crovol M70), PEG-60 almond oil (Crovol A70), PEG-40 palm kernel oil (Crovol PK70), PEG-50 castor oil (Emalex C-50), PEG-50 hydrogenated castor oil (Emalex HC-50), PEG-8 caprylic/capric glycerides (Labrasol), and PEG-6 caprylic/capric glycerides (Softigen 767). Preferred hydrophobic surfactants in this class include PEG-5 hydrogenated castor oil, PEG-7 hydrogenated castor oil, PEG-9 hydrogenated castor oil, PEG-corn oil (Labrifil M 2125 CS), Peg-6 almond oil (Labrifil M 1944 CS), PEG-6 olive oil (Labrifil M 1980 CS), PEG-6 peanut oil (Labrifil M 1969 CS), PEG-6 hydrogenated palm kernel oil (Labrifil M 2130 BS), PEG-6 triolein (Labrifil b M 2735 CS), PEG-8 corn oil (Labrifil WL 2609 BS), PEG-20 corn glycerides (Crovol M40), and PEG-20 almond glycerides (Crovel A40). The latter two surfactants are reported to have HLB values of 10, which is generally considered to be the approximate border line between hydrophilic and hydrophobic surfactants. For purposes of the present invention, these two surfactants are considered to by hydrophobic. Representative surfactants of this class suitable for use in the present invention are shown in Table 5.

TABLE 5

Transesterification Products of Oils and Alcohols

| Compound | Commercial Product (Supplier) | HLB |
|---|---|---|
| PEG-3 castor oil | Nikkol CO-3 (Nikko) | 3 |
| PEG-5, 9, and 16 castor oil | ACCONON CA series (ABITEC) | 6-7 |
| PEG-20 castor oil | Emalex C-20 (Nihon Emulsion), Nikkol CO-20 | 11 |
| PEG-23 castor oil | Emulgante EL23 | >10 |
| PEG-30 castor oil | Emalex C-30 (Nihon Emulsion), Alkamuls EL 620 (Rhone-Poulenc), Incrocas 30 (Croda) | 11 |
| PEG-35 castor oil | Cremophor EL and EL-P (BASF), Emulphor EL, Incrocas-35 (Croda), Emulgin RO 35 (Henkel) | N/A |
| PEG-38 castor oil | Emulgante EL 65 (Condea) | |
| PEG-40 castor oil | Emalex C-40 (Nihon Emulsion), Alkamuls EL 719 (Rhone-Poulenc) | 13 |
| PEG-50 castor oil | Emalex C-50 (Nihon Emulsion) | 14 |
| PEG-56 castor oil | Eumulgin PRT 56 (Pulcra SA) | >10 |
| PEG-60 castor oil | Nikkol CO-60TX (Nikko) | 14 |
| PEG-100 castor oil | Thornley | >10 |
| PEG-200 castor oil | Eumulgin PRT 200 (Pulcra SA) | >10 |
| PEG-5 hydrogenated castor oil | Nikkol HCO-5 (Nikko) | 6 |
| PEG-7 hydrogenated castor oil | Simusol 989 (Seppic), Cremophor WO7 (BASF) | 6 |
| PEG-10 hydrogenated castor oil | Nikkol HCO-10 (Nikko) | 6.5 |
| PEG-20 hydrogenated castor oil | Nikkol HCO-20 (Nikko) | 11 |
| PEG-25 hydrogenated castor oil | Simulsol 1292 (Seppic), Cerex ELS 250 (Auschem SpA) | 11 |
| PEG-30 hydrogenated castor oil | Nikkol HCO-30 (Nikko) | 11 |
| PEG-40 hydrogenated castor oil | Cremophor RH 40 (BASF), Croduret (Croda), Emulgin HRE 40 (Henkel) | 13 |
| PEG-45 hydrogenated castor oil | Cerex ELS 450 (Auschem Spa) | 14 |
| PEG-50 hydrogenated castor oil | Emalex HC-50 (Nihon Emulsion) | 14 |
| PEG-60 hydrogenated castor oil | Nikkol HCO060 (Nikko); Cremophor RH 60 (BASF) | 15 |
| PEG-80 hydrogenated castor oil | Nikkol HCO-80 (Nikko) | 15 |
| PEG-100 hydrogenated castor oil | Nikkol HCO-100 (Nikko) | 17 |
| PEG-6 corn oil | Labrafil M 2125 CS (Gattefosse) | 4 |
| PEG-6 almond oil | Labrafil M 1966 CS (Gattefosse) | 4 |
| PEG-6 apricot kernel oil | Labrafil M 1944 CS (Gattefosse) | 4 |
| PEG-6 olive oil | Labrafil M 1980 CS (Gattefosse) | 4 |
| PEG-6 peanut oil | Labrafil M 1969 CS (Gattefosse) | 4 |
| PEG-6 hydrogenated palm | Labrafil M 2130 BS (Gattefosse) | 4 |
| PEG-6 palm kernel oil | Labrafil M 2130 CS (Gattefosse) | 4 |
| PEG-6 triolein | Labrafil M 2735 CS (Gattefosse) | 4 |
| PEG-8 corn oil | Labrafil WL 2609 BS (Gattefosse) | 6-7 |
| PEG-20 corn glycerides | Crovol M40 (Croda) | 10 |
| PEG-20 almond glycerides | Crovo A40 (Croda) | 10 |
| PEG-25 trioleate | TAGAT TO (Goldschmidt) | 11 |
| PEG-40 palm kernel oil | Crovol PK-70 | >10 |
| PEG-60 corn glycerides | Crovol M70 (Croda) | 15 |
| PEG-60 almond glycerides | Crovol A70 (Croda) | 15 |
| PEG-4 caprylic/capric | Labrafac Hydro (Gattefosse) | 4-5 |
| PEG-8 caprylic/capric glycerides | Labrasol (Gattefosse), Labrafac CM 10 (Gattefosse) | >10 |

TABLE 5-continued

Transesterification Products of Oils and Alcohols

| Compound | Commercial Product (Supplier) | HLB |
|---|---|---|
| PEG-6 caprylic/capric glycerides | SOFTIGEN 767 (Huls), Glycerox 767 (Croda) | 19 |
| Lauroyl macrogol-32 glyceride | GELUCIRE 44/14 (Gattefosse) | 14 |
| Stearoyl macrogol glyceride | GELUCIRE 50/13 (Gattefosse) | 13 |
| Mono, di, tri, tetra esters of vegetable oils and sorbitol | SorbitolGlyceride (Gattefosse) | <10 |
| Pentaerythrityl tetraisostearate | Crodamol PTIS (Croda) | <10 |
| Pentaerythrityl distearate | Albunol DS (Taiwan Surf.) | >10 |
| Pentaerythrityl tetraoleate | Liponate PO-4 (Lipo Chem.) | >10 |
| Pentaerythrityl tetrastearate | Liponate PS-4 (Lipo Chem.) | <10 |
| Pentaerythrityl tetracaprylate/tetracaprate | Liponate PE-810 (Lipo Chem.), Crodamol PTC (Croda) | <10 |
| Pentaerythrityl tetraoctanoate | Nikkol Pentarate 408 (Nikko) | |

Also included as oils in this category of surfactants are oil-soluble vitamins, such as vitamins A, D, E, K, etc. Thus, derivatives of these vitamins, such as tocopheryl PEG-100 succinate (TPGS, available from Eastman), are also suitable surfactants.

6. Polyglycerized Fatty Acids

Polyglycerol esters of fatty acids are also suitable surfactants for the present invention. Among the polyglyceryl fatty acid esters, preferred hydrophobic surfactants include polyglyceryl oleate (Plurol Oleique), polyglyceryl-2 dioleate (Nikkol DGDO), and polyglyceryl-10 trioleate. Preferred hydrophilic surfactants include polyglyceryl-10 laurate (Nikkol Decaglyn 1-L), polyglyceryl-10 oleate (Nikkol Decaglyn 1-0), and polyglyceryl-10 mono, dioleate (Caprool PEG 860). Polyglyceryl polyricinoleates (Polymuls) are also preferred hydrophilic and hydrophobic surfactants. Examples of suitable polyglyceryl esters are shown in Table 6.

TABLE 6

Polyglycerized Fatty Acids

| Compound | Commercial Product (Supplier) | HLB |
|---|---|---|
| Polyglyceryl-2 stearate | Nikkol DGMS (Nikko) | 5-7 |
| Polyglyceryl-2 oleate | Nikkol DGMO (Nikko) | 5-7 |
| Polyglyceryl-2 isostearate | Nikkol DGMIS (Nikko) | 5-7 |
| Polyglyceryl-3 oleate | Caprol 3GO (ABITEC), Drewpol 3-1-O (Stepan) | 6.5 |
| Polyglyceryl-4 oleate | Nikkol Tetraglyn 1-O (Nikko) | 5-7 |
| Polyglyceryl-4 stearate | Nikkol Tetraglyn 1-S (Nikko) | 5-6 |
| Polyglyceryl-6 oleate | Drewpol 6-1-O (Stepan), Nikkol Hexaglyn 1-O (Nikko) | 9 |
| Polyglyceryl-10 laurate | Nikkol Decaglyn 1-L (Nikko) | 15 |
| Polyglyceryl-10 oleate | Nikkol Decaglyn 1-O (Nikko) | 14 |
| Polyglyceryl-10 stearate | Nikkol Decaglyn 1-S (Nikko) | 12 |
| Polyglyceryl-6 ricinoleate | Nikkol Hexaglyn PR-15 (Nikko) | >8 |
| Polyglyceryl-10 linoleate | Nikkol Decaglyn 1-LN (Nikko) | 12 |
| Polyglyceryl-6 pentaoleate | Nikkol Hexaglyn 5-O (Nikko) | <10 |
| Polyglyceryl-3 dioleate | Cremophor GO32 (BASF) | <10 |
| Polyglyceryl-3 distearate | Cremophor GS32 (BASF) | <10 |
| Polyglyceryl-4 pentaoleate | Nikkol Tetraglyn 5-O (Nikko) | <10 |
| Polyglyceryl-6 dioleate | Caprol 6G20 (ABITEC); Hodag PGO-62, (Calgene) PLUROL OLEIQUE CC 497 (Gattefosse) | 8.5 |
| Polyglyceryl-2 dioleate | Nikkol DGDO (Nikko) | 7 |
| Polyglyceryl-10 trioleate | Nikkol Decaglyn 3-O (Nikko) | 7 |
| Polyglyceryl-10 pentaoleate | Nikkol Decaglyn 5-O (Nikko) | 3.5 |
| Polyglyceryl-10 septaoleate | Nikkol Decaglyn 7-O (Nikko) | 3 |
| Polyglyceryl-10 tetraoleate | Caprol 10G40 (ABITEC; Hodag PGO-62 (CALGENE), Drewpol 10-4-O (Stepan) | |
| Polyglyceryl-10 decaisostearate | Nikkol Decaglyn 10-IS (Nikko) | <10 |
| Polyglyceryl-101 decaoleate | Drewpol 10-10-O (Stepan), Caprol 10G10O (ABITEC), Nikkol Decaglyn 10-O | 3.5 |
| Polyglyceryl-10 mono, dioleate | Caprol PGE 860 (ABITEC) | 11 |
| Polyglyceryl polyricinoleate | Polymuls (Henkel) | 3-20 |

7. Propylene Glycol Fatty Acid Esters

Esters of propylene glycol and fatty acids are suitable surfactants for use in the present invention. In this surfactant class, preferred hydrophobic surfactants include propylene glycol monolaurate (Lauroglycol FCC), propylene glycol ricinoleate (Propymuls), propylene glycol monooleate (Myverol P-06), propylene glycol dicaprylate/dicaprate (Captex 200), and propylene glycol dioctanoate (Captex 800). Examples of surfactants of this class are given in Table 7.

TABLE 7

Propylene Glycol Fatty Acid Esters

| Compound | Commercial Product (Supplier) | HLB |
|---|---|---|
| Propylene glycol monocaprylate | Capryol 90 (Gattefosse), Nikkol Sefsol 218 (Nikko) | <10 |
| Propylene glycol monolaurate | Lauroglycol 90 (Gattefosse), Lauroglycol FCC (Gattefosse) | <10 |
| Propylene glycol oleate | Lutrol OP2000 (BASF) | <10 |
| Propylene glycol myristate | Mirpyl | <10 |
| Propylene glycol monostearate | ADM PGME-03 (ADM), LIPO PGMS (Lipo Chem.), Aldo PGHMS (Lonza) | 3-4 |
| Propylene glycol hydroxyl stearate | | <10 |
| Propylene glycol ricinoleate | PROPYMULS (Henkel) | <10 |
| Propylene glycol isostearate | | <10 |
| Propylene glycol monooleate | Myverof P-06 (Eastman) | <10 |
| Propylene glycol dicaprylate/dicaprate | Captex 200 (ABITEC), Miglyol 840 (Huls), Neobee M-20 (Stepan) | <6 |
| Propylene glycol dioctanoate | Captex 800 (ABITEC) | <6 |
| Propylene glycol caprylate/caprate | LABRAFAC PG (Gattefosse) | >6 |
| Propylene glycol dilaurate | | >6 |
| Propylene glycol distearate | Kessco PGDS (Stepan) | >6 |
| Propylene glycol dicaprylate | Nikkol Sefsol 228 (Nikko) | >6 |
| Propylene glycol dicaprate | Nikkol PDD (Nikko) | |

8. Mixtures of Propylene Glycol Esters-Glycerol Esters

In general, mixtures of surfactants are also suitable for use in the present invention. In particular, mixtures of propylene glycol fatty acid esters and glycerol fatty acid esters are suitable and are commercially available. One preferred mixture is composed of the oleic acid esters of propylene glycol and glycerol (Arlacel 186). Examples or these surfactants are shown in Table 8.

TABLE 8

7/26 Glycerol/Propylene Glycol Fatty Acid Esters

| Compound | Commercial Product (Supplier) | HLB |
|---|---|---|
| Oleic | ATMOS 300, ARLACEL 186 (ICI) | 3-4 |
| Stearic | ATMOS 150 | 3-4 |

9. Mono-Diglycerides

A particularly important class of surfactants is the class of mono- and diglycerides. These surfactants are generally hydrophobic. Preferred hydrophobic surfactants in this class of compounds include glyceryl monooleate (Peceol), glyceryl ricinoleate, glyceryl laurate, glyceryl dilaurate (Capmul GDL), glyceryl dioleate (Capmul GDO), glyceryl mono/dioleate (Capmul GMO-K), glyceryl caprylate/caprate (Capmul MCM), caprylic acid mono/diglycerides (Imwitor 988), and mono- and diacetylated monoglycerides (Myvacet 9-45). Examples of these surfactants are given in Table 9.

TABLE 9

Mono- and Diglyceride Surfactants

| Compound | Commercial Product (Supplier) | HLB |
|---|---|---|
| Monopalmitolein (C16:1) | (Larodan) | <10 |
| Monoelaidin (C18:1) | (Larodan) | <10 |
| Monocaproin (C6) | (Larodan) | <10 |
| Monocaprylin | (Larodan) | <10 |
| Monocaprin | (Larodan) | <10 |
| Monolaurin | (Larodan) | <10 |
| Glyceryl monomyristate (C14) | Nikkol MGM (Nikko) | 3-4 |
| Glyceryl monooleate (C18:1) | PECEOL (Gattefosse), Hodag GMO-D, Nikkol MGO (Nikko) | 3-4 |
| Glyceryl monooleate | RYLO series (Danisco, DIMODAN series (Danisco), EMULDAN (Danisco), ALDO MO FH (Lonza), Kessco GMO (Stepan), MONOMULS series (Henkel), TEGIN O, DREWMULSE GMO (Stepan), Atlas G-695 (ICI), GMOrphic 80 (Eastman), ADM DMG-40, 70, and 100 (ADM), Myverol (Eastman) | |
| Glyceryl mono-oleate/linoleate | OLICINI (Gattefosse) | 3-4 |
| Glyceryl monolineate | Maisine (Gattefosse), MYVEROL 18-92, Myverol 18-06 (Eastman) | |
| Glyceryl ricinoleate | Softigen 701 (Huls), HODAG GMR-D (Calgene), ALDO MR (Lonza) | 6 |
| Glyceryl monolaurate | ALDO MLD (Lonza), Hodag GML (Calgene) | 6.8 |
| Glyceryl monopalmitate | Emalex GMS-P (Nihon) | 4 |
| Glyceryl monostearate | Capmul GMS (ABITEC), Myvaplex, IMWITOR 191 (Huls), CUTINA GMS, Aldo MS (Lonza), Nikkol MGS series (Nikko) | 5-9 |
| Glyceryl mono-, dioleate | Capmul GMO-K (ABITEC) | <10 |
| Glyceryl palmitic/stearic | CUTINA MD-A, ESTAGEL-G18 | <10 |
| Glyceryl acetate | Lamegin EE (Gunau GmbH) | <10 |
| Glyceryl laurate | Imwitor 312 (Huls), Monoluls 90-45 (Grunau GmbH), Aldo MLD (Lonza) | 4 |
| Glyceryl citrate/lactate/oleate/linoleate | Imwitor 375 (Huls) | <10 |
| Glyceryl caprylate | Imwitor 308 (Huls), Capmul MCMS (ABITEC) | 5-6 |
| Glyceryl caprylate/caprate | Capmul MCM (ABITEC) | 5-6 |
| Caprylic acid mono, diglycerides | Imwitor 988 (Huls) | 5-6 |
| Caprylic/capric glycerides | Imwitor 742 (Huls) | <10 |
| Mono- and monoglycerides | Myvacet 9-45, Myvacet 9-40, Myvacet 9-08 (Eastman), Lamegin (Grunau) | 3.8-4 |
| Glyceryl monostearate | Aldo MS, Arlacel 129 (ICI), LIPO GMS (Lipo Chem.), Imwitor 191 (Huls), Myvaplex (Eastman) | 4.4 |
| Lactic acid esters of mono, diclycerides | LAMEGIN GLP (Henkel) | <10 |
| Dicaproin (C6) | (Larodan) | <10 |
| Dacaprin (C10) | (Larodan) | <10 |
| Dioctanoin (C8) | (Larodan) | <10 |
| Dimyristin (C14) | (Larodan) | <10 |
| Dipalmitin (C16) | (Larodan) | <10 |
| Distearin | (Larodan) | <10 |
| Glyceryl dilaurate (C12) | Capmul GDL (ABITEC) | 3-4 |

TABLE 9-continued

Mono- and Diglyceride Surfactants

| Compound | Commercial Product (Supplier) | HLB |
|---|---|---|
| Glyceryl dioleate | Capmul GDO (ABITEC) | 3-4 |
| Glyceryl esters of fatty acids | GELUCIRE 39/01 (Gattefosse), GELUCIRE 43/01 (Gattefosse), GELUCIRE 37/06 (Gattefosse) | 6 |
| Dipalmitolein (C16:1) | (Larodan) | <10 |
| 1,2 and 1,3-diolein (C18:1) | (Larodan) | <10 |
| Dielaidin (C18:1) | (Larodan) | <10 |
| Dilinolein (C18:2) | (Larodan) | <10 |

10. Sterol and Sterol Derivatives

Sterols and derivatives of sterols are suitable surfactants for use in the present invention. These surfactants can be hydrophilic or hydrophobic. Preferred derivatives include the polyethylene glycol derivatives. A preferred hydrophobic surfactant in this class is cholesterol. A preferred hydrophilic surfactant in this class is PEG-24 cholesterol ether (Solulan C-24). Examples of surfactants of this class are shown in Table 10.

TABLE 10

Sterol and Sterol Derivative Surfactant

| Compound | Commercial Product (Supplier) | HLB |
|---|---|---|
| Cholesterol, sitosterol, Ianosterol | | <10 |
| PEG-24 cholesterol ether | Solulan C-24 (Amerchol) | >10 |
| PEG-30 cholestanol | Nikkol DHC (Nikko) | >10 |
| Phytosterol | GENEROL series (Henkel) | <10 |
| PEG-25 phyto sterol | Nikkol BPSH-25 (Nikko) | >10 |
| PEG-5 soya sterol | Nikkol BPS-5 (Nikko) | <10 |
| PEG-10 soya sterol | Nikkol BPS-10 (Nikko) | <10 |
| PEG-20 soya sterol | Nikkol BPS-20 (Nikko) | <10 |
| PEG-30 soya sterol | Nikkol BPS-30 (Nikko) | >10 |

11. Polyethylene Glycol Sorbitan Fatty Acid Esters

A variety of PEG-sorbitan fatty acid esters are available and are suitable for use as surfactants in the present invention. In general, these surfactants are hydrophilic, although several hydrophobic surfactants of this class can be used. Among the PEG-sorbitan fatty acid esters, preferred hydrophilic surfactants include PEG-20 sorbitan monolaurate (Tween-20), PEG-20 sorbitan monostearate (Tween-60), and PEG-20 sorbitan monooleate (Twee-80). Examples of these surfactants are shown in Table 11.

TABLE 11

PEG-Sorbitan Fatty Acid Esters

| Compound | Commercial Product (Supplier) | HLB |
|---|---|---|
| PEG-10 sorbitan laurate | Liposorb L-10 (Lipo Chem.) | >10 |
| PEG-20 sorbitan monolaurate | Tween-20 (Atlas/ICI), Crillet 1 (Croda), DACOL MLS 20 (Condea) | 17 |
| PEG-4 sorbitan monolaurate | Tween-21 (Atlas/ICI), Crillet 11 (Croda) | 13 |
| PEG-80 sorbitan monolaurate | Hodag PSML-80 (Calgene); T-Maz 28 | >10 |
| PEG-6 sorbitan | Nikkol GL-1 (Nikko) | 16 |
| PEG-20 sorbitan monopalmitate | Tween 40 (Atlas/ICI), Crillet 2 (Croda) | 16 |
| PEG-20 sorbitan monostearate | Tween-60 (Atlas/ICI), Crillet 3 (Croda) | 15 |
| PEGA sorbitan monostearate | Tween-61 (Atlas/ICI), Crillet 31 (Croda) | 9.6 |

TABLE 11-continued

PEG-Sorbitan Fatty Acid Esters

| Compound | Commercial Product (Supplier) | HLB |
|---|---|---|
| PEG-8 sorbitan monostearate | DACOL MSS (Condea) | >10 |
| PEG-6 sorbitan monostearate | Nikkol TS106 (Nikko) | 11 |
| PEG-20 sorbitan tristearate | Tween-65 (Atlas/ICI), Crillet 35 (Croda) | 11 |
| PEG-6 sorbitan tetrastearate | Nikkol GS-6 (Nikko) | 3 |
| PEG-60 sorbitan tetrastearate | Nikkol GS-460 (Nikko) | 13 |
| PEG-5 sorbitan monooleate | Tween-81 (Atlas/ICI), Crillet 41 (Croda) | 10 |
| PEG-6 sorbitan monooleate | Nikkol TO-106 (Nikko) | 10 |
| PEG-20 sorbitan monooleate | Tween-80 (Atlas/ICI), Crillet 4 (Croda) | 15 |
| PEG-40 sorbitan oleate | Emalex ET 8040 (Nihon Emulsion) | 18 |
| PEG-20 sorbitan trioleate | Tween-85 (Atlas/ICI), Crillet 45 (Croda) | 11 |
| PEG-6 sorbitan tetraoleate | Nikkol GO-4 (Nikko) | 8.5 |
| PEG-30 sorbitan tetraoleate | Nikkol G-430 (Nikko) | 12 |
| PEG-40 sorbitan tetraoleate | Nikkol GO-440 (Nikko) | 13 |
| PEG-20 sorbitan monoisostearate | Tween-120 (Atlas/ICI), Crillet 6 (Croda) | >10 |
| PEG sorbitol hexaoleate | Atlas G-1086 (ICI) | 10 |
| PEG-6 sorbitol hexastearate | Nikkol GS-6 (Nikko) | 3 |

12. Polyethylene Glycol Alkyl Ethers

Ethers of polyethylene glycol and alkyl alcohols are suitable surfactants for use in the present invention. Preferred hydrophobic ethers include PEG-3 oleyl ether (Volpo 3) and PEG-4 lauryl ether (Brij 30). Examples of these surfactants are shown in Table 12.

TABLE 12

Polyethylene Glycol Alkyl Ethers

| Compound | Commercial Product (Supplier) | HLB |
|---|---|---|
| PEG-2 oleyl ether, oleth-2 | Brij 92/93 (Atlas/ICI) | 4.9 |
| PEG-3 oleyl ether, oleth-3 | Volpo 3 (Croda) | <10 |
| PEG-5 oleyl ether, oleth-5 | Volpo 5 (Croda) | <10 |
| PEG-10 oleyl ether, oleth-10 | Volpo 10 (Croda), Brij 96/97 (Atlas/ICI) | 12 |
| PEG-20 oleyl ether, oleth-20 | Volpo 20 (Croda), Brij 98/99 (Atlas/ICI) | 15 |
| PEG-4 lauryl ether, laureth-4 | Brij 30 (Atlas/ICI) | 9.7 |
| PEG-9 lauryl ether | | >10 |
| PEG-23 lauryl ether, laureth-23 | Brij 35 (Atlas/ICI) | 17 |
| PEG-2 cetyl ether | Brij 52 (ICI) | 5.3 |
| PEG-10 cetyl ether | Brij 56 (ICI) | 13 |
| PEG-20 cetyl ether | Brij 58 (ICI) | 16 |
| PEG-2 stearyl ether | Brij 72 (ICI) | 4.9 |
| PEG-10 stearyl ether | Brij 76 (ICI) | 12 |
| PEG-20 stearyl ether | Brij 78 (ICI) | 1 |
| PEG-100 stearyl ether | Brij 100 (ICI) | >10 |

13. Sugar Esters

Esters of sugar are suitable surfactants for usein the present invention. Preferred hydrophilic surfactants in this class include sucrose monopalmitate and sucrose monolaurate. Examples of such surfactants are shown in Table 13.

TABLE 13

Sugar Ester Surfactants

| Compound | Commercial Product (Supplier) | HLB |
|---|---|---|
| Sucrose distearate | SUCRO ESTER 7 (Gattefosse), Crodesta F-10 (Croda) | 3 |
| Sucrose distearate/monostearate | SUCRO ESTER 11 (Gattefosse), Crodesta F-110 (Croda) | 12 |
| Sucrose dipalmitate | | 7.4 |
| Sucrose monostearate | Crodesta F-160 (Croda) | 15 |
| Sucrose monopalmitate | SUCRO ESTER 15 (Gattefosse) | >10 |
| Sucrose monolaurate | Saccharose monolaurate 1695 (Mitsubishi-Kasei) | 15 |

14. Polyethylene Glycol Alkyl Phenols

Several hydrophilic PEG-alkyl phenol surfactants are available, and are suitable for use in the present invention. Examples of these surfactants are shown in Table 14.

TABLE 14

Polyethylene Glycol Alkyl Phenol Surfactants

| Compound | Commercial Product (Supplier) | HLB |
|---|---|---|
| PEG-10-100 nonyl phenol | Triton X series (Rohm & Haas), Igepal CA series (GAF, USA), Antarox CA series (GAF, UK) | >10 |
| PEG-15-100 octyl phenol ether | Triton N-series (Rohm & Haas), Igepal CO series (GAF, USA), Antarox CO series (GAF, UK) | >10 |

15. Polyoxyethylene-Polyoxypropylene Block Copolymers

The POE-POP block copolymers are a unique class of polymeric surfactants. The unique structure of the surfactants, with hydrophilic POE and hydrophobic POP moieties in well-defined ratios and positions, provides a wide variety of surfactants suitable for use in the present invention. These surfactants are available under various trade names, including Synperonic PE series (ICI); Pluronic series (BASF), Emkalyx, Lutrol (BASF), Supronic, Monolan, Pluracare, and Plurodac. The generic term for these polymers is "poloxamer" (CAS 9003-11-6). These polymers have the formula: $HO(C_2H_4O)_a(C_3H_6O)_b(C_2H_4O)_aH$ where "a" and "b" denote the number of polyoxyethylene and polyoxypropylene units, respectively. Preferred hydrophilic surfactants of this class include Poloxamers, 108, 188, 217, 238, 288, 338, and 407. Preferred hydrophobic surfactants in this class include Poloxamers 124, 182, 183, 212, 331, and 335. Examples of suitable surfactants of this class are shown in Table 15. Since the compounds are widely available, commercial sources are not listed in the Table. The compounds are listed by generic name, with the corresponding "a" and "b" values.

TABLE 15

POE-POP Block Copolymers

| Compound | a, b values in $HO(C_2H_4O)_a(C_3H_6O)_b(C_2H_4O)_aH$ | | HLB |
|---|---|---|---|
| Poloxamer 105 | a = 11 | b = 16 | 8 |
| Poloxamer 108 | a = 46 | b = 16 | >10 |
| Poloxamer 122 | a = 5 | b = 21 | 3 |
| Poloxamer 123 | a = 7 | b = 21 | 7 |
| Poloxamer 123 | a = 11 | b = 21 | >7 |
| Poloxamer 181 | a = 3 | b = 30 | |
| Poloxamer 182 | a = 8 | b = 30 | 2 |
| Poloxamer 183 | a = 10 | b = 30 | |
| Poloxamer 184 | a = 13 | b = 30 | |
| Poloxamer 185 | a = 19 | b = 30 | |
| Poloxamer 188 | a = 75 | b = 30 | 29 |
| Poloxamer 212 | a = 8 | b = 35 | |
| Poloxamer 215 | a = 24 | b = 35 | |
| Poloxamer 217 | a = 52 | b = 35 | |
| Poloxamer 231 | a = 16 | b = 39 | |
| Poloxamer 234 | a = 22 | b = 39 | |
| Poloxamer 235 | a = 27 | b = 39 | |
| Poloxamer 237 | a = 62 | b = 39 | 24 |
| Poloxamer 238 | a = 97 | b = 39 | |
| Poloxamer 282 | a = 10 | b = 47 | |
| Poloxamer 284 | a = 21 | b = 47 | |
| Poloxamer 288 | a = 122 | b = 47 | >10 |
| Poloxamer 331 | a = 7 | b = 54 | 0.5 |
| Poloxamer 333 | a = 20 | b = 54 | |
| Poloxamer 334 | a = 31 | b = 54 | |
| Poloxamer 335 | a = 38 | b = 54 | |
| Poloxamer 338 | a = 128 | b = 54 | |
| Poloxamer 401 | a = 6 | b = 67 | |
| Poloxamer 402 | a = 13 | b = 67 | |
| Poloxamer 403 | a = 21 | b = 67 | |
| Poloxamer 407 | a = 98 | b = 67 | |

16. Sorbitan Fatty Acid Esters

Sorbitan esters of fatty acids are suitable surfactants for use in the present invention. Among these esters, preferred hydrophobic surfactants include sorbitan monolaurate (Arlacel 20), sorbitan monopalmitate (Span-40), sorbitan monooleate (Span-80), sorbitan monostearate, and sorbitan tristearate. Examples of these surfactants are shown in Table 16.

TABLE 16

Sorbitan Fatty Acid Esters Surfactants

| Compound | Commercial Product (Supplier) | HLB |
|---|---|---|
| Sorbitan monolaurate | Span-20 (Atlas/ICI), Crill 1 (Croda), Arlacel 20 (ICI) | 8.6 |
| Sorbitan monopalmitate | Span-40 (Atlas/ICI), Crill 2 (Croda), Nikkol SP-10 (Nikko) | 6.7 |
| Sorbitan monooleate | Span-80 (Atlas/ICI), Crill 4 (Croda), Crill 50 (Croda) | 4.3 |
| Sorbitan monostearate | Span-60 (Atlas/ICI), Crill 3 (Croda), Nikkol SS-10 (Nikko) | 4.7 |
| Sorbitan trioleate | Span-85 (Atlas/ICI), Crill 45 (Croda), Nikkol SO-30 (Nikko) | 4.3 |
| Sorbitan sesquioleate | Arlacel-C (ICI), Crill 43 (Croda), Nikkol SO-15 (Nikko) | 3.7 |
| Sorbitan tristearate | Span-65 (Atlas/ICI) Crill 35 (Croda), Nikkol SS-30 (Nikko) | 2.1 |
| Sorbitan monoisostearate | Crill 6 (Croda), Nikkol SI-10 (Nikko) | 4.7 |
| Sorbitan sesquistearate | Nikkol SS-15 (Nikko) | 4.2 |

17. Lower Alcohol Fatty Acid Esters

Esters of lower alcohols ($C_2$ to $C_4$) and fatty acids ($C_8$ to $C_{18}$) are suitable surfactants for use in the present invention. Among these esters, preferred hydrophobic surfactants include ethyl oleate (Crodamol EO), isopropyl myristate (Crodamol IPM), and isopropyl palmitate (Crodamol IPP). Examples of these surfactants are shown in Table 17.

TABLE 17

Sorbitan Fatty Acid Esters Surfactants

| Compound | Commercial Product (Supplier) | HLB |
| --- | --- | --- |
| Ethyl oleate | Crodamol EO (Croda), Nikkol EOO (Nikko) | <10 |
| Isopropyl myristate | Crodamol IPM (Croda) | <10 |
| Isopropyl palmitate | Crodamol IPP (Croda) | <10 |
| Ethyl linoleate | Nikkol VF-E (Nikko) | <10 |
| Isopropyl linoleate | Nikkol VF-IP (Nikko) | <10 |

18. Ionic Surfactants

Ionic surfactants, including cationic, anionic and zwitterionic surfactants, are suitable hydrophilic surfactants for use in the present invention. Preferred anionic surfactants include fatty acid salts and bile salts. Specifically, preferred ionic surfactants include sodium oleate, sodium lauryl sulfate, sodium lauryl sarcosinate, sodium dioctyl sulfosuccinate, sodium cholate, and sodium taurocholate. Examples of such surfactants are shown in Table 18 below. For simplicity, typical counterions are shown in the entries in the Table. It will be appreciated by one skilled in the art; however, that any bio-acceptable counterion may be used. For example, although the fatty acids are shown as sodium salts, other cation counterions can also be used, such as alkali metal cations or ammonium. Unlike typical non-ionic surfactants, these ionic surfactants are generally available as pure compounds, rather than commercial (proprietary) mixtures. Because these compounds are readily available from a variety of commercial suppliers, such as Aldrich Sigma, and the like, commercial sources are not generally listed in the Table.

TABLE 18

Ionic Surfactants

| Compound | HLB |
| --- | --- |
| FATTY ACID SALTS | >10 |
| Sodium caproate | |
| Sodium caprylate | |
| Sodium caprate | |
| Sodium laurate | |
| Sodium myristate | |
| Sodium myristolate | |
| Sodium palmitate | |
| Sodium palmitoleate | |
| Sodium oleate | 18 |
| Sodium ricinoleate | |
| Sodium linoleate | |
| Sodium linolenate | |
| Sodium stearate | |
| Sodium lauryl sulfate (dodecyl) | 40 |
| Sodium tetradecyl sulfate | |
| Sodium lauryl sarcosinate | |
| Sodium dioctyl sulfosuccinate (sodium docusate (Cytec)) | |
| BILE SALTS | >10 |
| Sodium cholate | |
| Sodium taurocholate | |
| Sodium glycocholate | |
| Sodium deoxycholate | |
| Sodium taurodeoxycholate | |
| Sodium glycodeoxycholate | |
| Sodium ursodeoxycholate | |
| Sodium chenodeoxycholate | |
| Sodium taurochenodeoxycholate | |
| Sodium glycol cheno deoxycholate | |
| Sodium cholylsarcosinate | |
| Sodium N-methyl taurocholate | |
| PHOSPHOLIPIDS | |
| Egg/Soy lecithin (Epikuron (Lucas Meyer), Ovothin (Lucas Meyer)) | |
| Lyso egg/soy lecithin | |
| Hydroxylated lecithin | |

TABLE 18-continued

Ionic Surfactants

| Compound | HLB |
| --- | --- |
| Lysophosphatidylcholine | |
| Cardiolipin | |
| Sphingomyelin | |
| Phosphatidylcholine | |
| Phosphatidyl ethanolamine | |
| Phosphatidic acid | |
| Phophatidyl glycerol | |
| Phosphatidyl serine | |
| PHOSPHORIC ACID ESTERS | |
| Diethanolammonium polyoxyethylene-10 oleyl ether phosphate | |
| Esterification products of fatty alcohols or fatty alcohol ethoxylates with phosphoric acid or anhydride | |
| CARBOXYLATES | |
| Ether carboxylates (by oxidation of terminal OH group of fatty alcohol ethoxylates) | |
| Succinylated monoglycerides (LAMEGIN ZE (Henkel)) | |
| Sodium stearyl fumarate | |
| Stearoyl propylene glycol hydrogen succinate | |
| Mono/diacetylated tartaric acid esters of mono- and diglycerides | |
| Citric acid esters of mono-, diglycerides | |
| Glyceryl-lacto esters of fatty acids (CFR ref. 172.852) | |
| Acyl lactylates | |
| lactylic esters of fatty acids | |
| calcium/sodium stearoyl-2-lactylate | |
| calcium/sodium stearoyl lactylate | |
| Alginate salts | |
| Propylene glycol alginate | |
| SULFATES AND SULFONATES | |
| Ethoxylated alkyl sulfates | |
| Alkyl benzene sulfones | |
| -olefin sulfonates | |
| Acyl isethionates | |
| Acyl taurates | |
| Alkyl glyceryl ether sulfonates | |
| Octyl sulfosuccinate disodium | |
| Disodium undecyclenamideo-MEA-sulfosuccinate | |
| CATIONIC Surfactants | >10 |
| Hexadecyl triammonium bromide | |
| Decyl trimethyl ammonium bromide | |
| Cetyl trimethyl ammonium bromide | |
| Dodecyl ammonium chloride | |
| Alkyl benzyldimenthylammonium salts | |
| Diisobutyl phenoxyethoxydimethyl benzylammonium salts | |
| Alkylpyridinium salts | |
| Betaines (trialkylglycine): | |
| Lauryl betaine (N-lauryl, N,N-dimenthylglycine) | |
| Ethoxylated amines: | |
| Polyoxyethylene-15 coconut amine | |

Examples of additional suitable solubilizer include: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol, available commercially from BASF under the trade name Tetraglycol) or methoxy PEG (Union Carbide); amides, such as 2-pyrrolidone, 2-piperidone, caprolactam, N-alkylpyrrolidone, N-hydroxyalkylpyrrolidone, N-alkylpiperidone, N-alkylcaprolactam, dimethylacetamide, and polyvinypyrrolidone; esters, such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, caprolactone and isomers thereof, valerolactone and isomers thereof, butyrolactone and isomers thereof; and other solubilizers known in the art, such as dimethyl acetamide, dimethyl isosorbide (Arlasolve DMI (ICI)), N-methylpyrrolidones (Pharmasolve (ISP)), monooctanoin, diethylene glycol nonoethyl ether (available from Gattefosse under the trade name Transcutol), and water. Mixtures of solubilizers are also within the scope of the invention.

Except as indicated, compounds mentioned herein are readily available from standard commercial sources.

Particularly suitable water miscible solvents include, by way of example and without limitation, ethanol or iso-propyl alcohol, poly(ethylene glycol). Particularly suitable emulsifying agents include, by way of example and without limitation, is glycerol monooleate, vitamin E TPGS, Gelucire, Cremophor, Labrafil, poloxamer and Labrasol. Particularly suitable water immiscible solvents include, by way of example and without limitation, medium chain triglycerides and oleic aicd. Particularly suitable antioxidants include, by way of example and without limitation, vitamin E, BHT, or vitamin C palmitate.

Selection of excipients suitable for use in the solubilizer was conducted according to Example 4, Method A. Some of the suitable excipients include triglycerides of unsaturated fatty acids. These compounds are susceptible to oxidation, so an antioxidant is preferably included therewith in a composition of the invention. It is noted that even though a solubilizer (which is an excipient) might not be suitable for individually solubilizing the SCF extract, such an excipient can be used in a composition as a mixture with one or more other excipients that solubilize the SCF extract.

A pharmaceutical liquid composition of the invention can be clear or a suspension. Clarity of the liquid composition was determined visually with the unaided eye or with a microscope using the method of Example 5. The clear liquid composition is visually clear to the unaided eye, as it will contain less than 5%, less than 3% or less than 1% by wt. of suspended solids based upon the total weight of the composition. Specific embodiments of the invention include a pharmaceutical clear liquid composition that can be used as a fill composition in a capsule thereby forming a liquid filled capsule formulation. The clear liquid composition is made by mixing the SCF extracts with a solubilizer of the invention, optionally in the presence of heat, wherein the solubilizer is present in an amount sufficient to dissolve the extract.

Exemplary liquid compositions of the invention are described in Example 3. The composition of Example 3, Method A is a cremophor-based drug delivery system. The composition of Example 3, Method B is a GMO (glycerol monooleate)/cremophor-based drug delivery system. The composition of Example 3, Method C is a labrasol-based micelle forming system. Each of these formulations includes an antioxidant since the surfactant excipient contains unsaturated fatty acid, which is a solubilizing agent. They also include ethanol as a water soluble (miscible) solvent.

As used herein, the term "micelle forming system" refers to a composition that forms a micellar dispersion or emulsion when placed in an aqueous medium. As used herein, the term "self-emulsifying system" refers to a composition that forms an emulsion when placed in an aqueous medium.

The composition of Example 3, Method D is a Vitamin E TPGS based drug delivery system.

The dissolution properties of the formulation, when placed in an aqueous medium, were evaluated according to Example 4, Method C. When the composition of Example 3, Method A was placed in phosphate buffer (pH 6.8), micelles formed and the composition dissolved in the buffer. When the composition of Example 3, Method B was placed in phosphate buffer (pH 6.8), the composition dispersed in the buffer. When the liquid composition of Example 3, Method C was placed in phosphate buffer (pH 6.8), the formation of fine particles in the buffer was observed. When the composition of Example 3, Method D was placed in phosphate buffer (pH 6.8), a micellular dispersion was formed.

If desired the liquid composition can be sterilized by: 1) sterile filtering the fill composition through a filtration medium wherein the pore size is about 0.22 µm or smaller; 2) irradiating the fill composition; 3) treating the fill composition with ethylene oxide; 4) purging the fill composition with an inert gas to reduce the amount of dissolved oxygen therein; and/or 5) heating the fill composition.

A capsule formulation comprises a shell, a pharmaceutical liquid composition filling, and optionally, an enteric coat. A capsule according to the invention will have a storage shelf-life of no less than one week, three weeks, one month, three months, six months, or one year. For example, for a capsule having a shelf life of at least six months, the shell of the capsule will not fail storage stability tests for a storage period of at least six months. The criteria for acceptable shelf-life are set as needed according to a given capsule product and its storage stability requirements. It should be noted that a shelf-life of as little as one week is suitable for products that are compounded by a pharmacist and sold to customers of a pharmacy.

The loading or filling of a liquid composition into a capsule can be achieved by any known method for preparing liquid, gel, semi-solid or solid melt filled capsules. In particular, the methods described by R. P. Scherer company, Alza or MW Encap Ltd. can be used. One exemplary method is described by Bowtle (*Pharmaceutical Technology Europe* (1998), 10 (10), 84,86, 88-90.

The term "shell" as used herein is taken to mean the shell of a capsule dosage form or the encasement or encapsulation material used to encapsulate fill compositions made from the particles. Any material suitable for use in forming a capsule shell or in encapsulating another composition can be used according to the invention.

The shell can be hard or soft and any materials suitable for preparing such shells can be used in the capsule of the invention. Materials suitable for the preparation of the capsule shell include soft gelatin, hard gelatin, hydroxypropyl methylcellulose, starch, animal gelatin, agar, fish (piscine) gelatin or a combination thereof. Other suitable materials include: polyinyl alcohol/polyvinyl acetate copolymer (U.S. Pat. No. 3,300, 546); a blend of hydroxybutyl methylcellulose and hydroxypropyl methylcellulose (U.S. Pat. No. 4,765,916); polyvinyl acetate (U.S. Pat. Nos. 2,560,649, No. 3,346,502); water-soluble gelatin (U.S. Pat. No. 3,525,426); polyvinyl alcohol (U.S. Pat. Nos. 3,528,921, 3,534,851, 3,556,765, 3,634,260, 3,671,439, 3,706,670, 3,857,195, 3,877,928, 4,367,156, 4,747,976, 5,270,054); polymers derived from such monomers as vinyl chloride, vinyl alcohol, vinyl pyrrolidone, furan, acrylonitrile, vinyl acetate, methyl acrylate, methyl methacrylate, styrene, vinyl ethyl ether, vinyl propyl ether, acrylamide, ethylene, propylene, acrylic acid, methacrylic acid, maleic anhydride, salts of any of the aforementioned acids and mixtures thereof; polyvinyl chloride; polypropylene; acrylic/maleic copolymers; sodium polyacrylate; polyvinyl pyrrolidone; glucomannan and optionally another natural polysaccharide with a polyhydric alcohol such as glycerin (U.S. Pat. No. 4,851,394); plastic and polylactide/polyglycolide (Elanco Animal Health Co.); HPMC (Shionogi Qualicaps Co. Ltd (Nara Japan); SUHEUNG CAPSULES CO. LTD. (KYUNGGI-DO, KOREA) and Capsugel); or a combination thereof. Essentially any material known to those of ordinary skill in the art as being for the preparation of capsule shell can be used in a capsule according to the invention.

Suitable starch capsules can be made and used according to Vilivalam et al. (*Pharmaceutical Science & Technology Today* (2000), 3 (2), 64-69). A chitosan capsule for colonic delivery can be made and used according to Yamamoto (*Kobunshi* (1999), 48 (8), 595) or Tozaki et al. (*Drug Delivery System* (1997), 12 (5), 311-320). Other suitable shell materials are disclosed in U.S. Patent Application Publication No. 2002/0081331 to R. P. Scherer Technologies Inc. (Cardinal Health, Inc.), which discloses film-forming compositions comprising modified starches and iota-carrageenan.

The capsule of the invention can also be coated with an enteric coat to delay release of its contents until it is downstream from the gastric region following oral administration or until it is exposed to an aqueous medium having a pH of at least about 5. An enteric coated capsule can be adapted to release the liquid composition in the duodenum, jejunum, ileum, small intestine or large intestine.

The enteric coat (delayed release coat) is exterior to and surrounds (encloses or envelopes) the capsule shell. The coating is insoluble in the fluid of a first environment of use, such as gastric juices, acidic fluids, and soluble or erodible in the fluid of a second environment of use, such as intestinal juices, substantially pH neutral or basic fluids, or mildly acidic (pH of 5 or greater) fluids. Many polymeric materials are known to possess these various solubility properties and can be included in the enteric coat. Such other polymeric materials include, by way of example and without limitation, cellulose acetate phthalate (CAP), cellulose acetate trimelletate (CAT), poly(vinyl acetate) phthalate (PVAP), hydroxypropylmethylcellulose phthalate (HP), poly(methacrylate ethylacrylate) (1:1) copolymer (MA-EA), poly(methacrylate methylmethacrylate) (1:1) copolymer (MA-MMA), poly(methacrylate methylmethacrylate) (1:2) copolymer, Eudragit L-30D™ (MA-EA, 1:1), Eudragit L-100-55™ (MA-EA, 1:1), hydroxypropylmethylcellulose acetate succinate (HPMCAS), Coateric™ (PVAP), Aquateric™ (CAP), AQOATT™ (HPMCAS) and combinations thereof.

When the enteric coat is intended to be dissolved, eroded or become detached from the capsule in the colon, materials such as hydroxypropylcellulose, microcrystalline cellulose (MCC, Avicel™ from FMC Corp.), poly(ethylene-vinyl acetate) (60:40) copolymer (EVAC from Aldrich Chemical Co.), 2-hydroxyethylmethacrylate (HEMA), MMA, terpolymers of HEMA: MMA:MA synthesized in the presence of N,N'-bis(methacryloyloxyethyloxycarbonylamino)-azobenzene, azopolymers, enteric coated timed release system (Time Clock® from Pharmaceutical Profiles, Ltd., UK) and calcium pectinate can be included in the coat.

The enteric coat can comprise one or more materials that do not dissolve, disintegrate, or erode in the stomach and during the period of time that the capsule resides in the stomach. A material that easily adapts to this kind of requirement is a poly(vinylpyrrolidone)-vinyl acetate copolymer, such as the material supplied by BASF under its Kollidon VA64 trademark. The enteric coat can also comprise povidone, which is supplied by BASF under its Kollidon K 30 trademark, and hydroxypropyl methylcellulose, which is supplied by Dow under its Methocel E-15 trademark.

The enteric coat can also comprise other materials suitable which are substantially resistant to gastric juices and which will promote either enteric or colonic release. Representative materials that keep their integrity in the stomach can comprise a member selected from the group consisting of (a) keratin, keratin sandarac-tolu, salol (phenyl salicylate), salol beta-naphthylbenzoate and acetotannin, salol with balsam of Peru, salol with tolu, salol with gum mastic, salol and stearic acid, and salol and shellac; (b) a member selected from the group consisting of formalized protein, formalized gelatin, and formalized cross-linked gelatin and exchange resins; (c) a member selected from the group consisting of myristic acid-hydrogenated castor oil-cholesterol, stearic acid-mutton tallow, stearic acid-balsam of tolu, and stearic acid-castor oil; (d) a member selected from the group consisting of shellac, ammoniated shellac, ammoniated shellac-salol, shellac-wool fat, shellac-acetyl alcohol, shellac-stearic acid-balsam of tolu, and shellac n-butyl stearate; (e) a member selected from the group consisting of abietic acid, methyl abictate, benzoin, balsam of tolu, sandarac, mastic with tolu, and mastic with tolu, and mastic with acetyl alcohol; (f) acrylic resins represented by anionic polymers synthesized from methacrylate acid and methacrylic acid methyl ester, copolymeric acrylic resins of methacrylic and methacrylic acid and methacrylic acid alkyl esters, copolymers of alkacrylic acid and alkacrylic acid alkyl esters, acrylic resins such as dimethylaminoethyl-methacrylate-butylmethacrylate-methylmethacrylate copolymer of 150,000 molecular weight, methacrylic acid-methylmethacrylate 50:50 coploymer of 135,000 molecular weight, methacrylic acid-methylmethacrylate-30:70-copolymer of 135,000 mol. wt., methacrylic acid-dimethylaminoethyl-methacrylate-ethylacrylate of 750,000 mol. wt., methacrylic acid-methylmethacrylate-ethylacrylate of 1,000,000 mol. wt., and ethylacrylate-methylmethacrylate-ethylacrylate of 550,000 mol. wt; and, (g) an enteric composition comprising a member selected from the group consisting of cellulose acetyl phthalate, cellulose diacetyl phthalate, cellulose triacetyl phthalate, cellulose acetate phthalate, hydroxypropylmethylcellulose phathalate, sodium cellulose acetate phthalate, cellulose ester phthalate, cellulose ether phthalate, methylcellulose phthalate, cellulose ester-ether phthalate, hydroxypropyl cellulose phthalate, alkali salts of cellulose acetate phthalate, alkaline earth salts of cellulose acetate phthalate, calcium salt of cellulose acetate phthalate, ammonium salt of hydroxypropyl methylcellulose phthalate, cellulose acetate hexahydrophthalate, hydroxypropyl methylcellulose hexahydrophthalate, polyvinyl acetate phthalate diethyl phthalate, dibutyl phthalate, dialkyl phthalate wherein the alkyl comprises from 1 to 7 straight and branched alkyl groups, aryl phthalates, and other materials known to one or ordinary skill in the art.

Plasticizers that can be used in the coating(s), e.g. enteric coat or finish coat, of the capsule include all those that are generally incorporated into polymeric coatings of drug delivery devices. Plasticizers generally improve the mechanical properties and increase the flexibility of the polymeric film. Plasticizers generally reduce cohesive intermolecular forces and increase mobility of polymer chains, thus reducing polymer-polymer interactions. This action is responsible for the changes to the properties of the polymers and films thereof such as a reduction of Tg (glass transition temperature) or softening temperature and the elastic module, increasing polymer flexibility, thus facilitating the process of formation of the membrane or film. A preferred pharmaceutical plasticizer is non-toxic and non-irritating; has a reduced tendency to migrate, extrude or volatilize; and has good miscibility with the polymer(s) in the film. Plasticizers that can be used in the coating include, for example and without limitation, acetyl triethyl citrate, acetyl tributyl citrate, triethyl citrate, acetylated monoglycerides, glycerol, polyethylene glycol, triacetin, propylene glycol, dibutyl phthalate, diethyl phthalate, isopropyl phthalate, dimethyl phthalate, dactyl phthalate, dibutyl sebacate, dimethyl sebacate, castor oil, glycerol monostearate, fractionated coconut oil, poly(ethylene glycol) (PEG), others or a combination thereof. In some embodiments, the plasticizer is PEG having a molecular weight of 200 to 8000, ester of citric acid, ester of phthalic acid. Specific plasticizers include PEG having a molecular weight of 200 to 8000, triethyl citrate, tributyl citrate, diethyl phthalate, and dibutyl sebacate.

Suitable plasticizers also include, by way of example and without limitation, low molecular weight polymers, oligomers, copolymers, oils, small organic molecules, low molecular weight polyols having aliphatic hydroxyls, ester-type plasticizers, glycol esters, poly(propylene glycol), multi-block polymers, single-block polymers, low molecular weight poly(ethylene glycol), citrate ester-type plasticizers, triacetin, propylene glycol and glycerin. Such plasticizers can also include ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, acetyltributylcitrate, triethyl citrate, acetyl triethyl citrate, tributyl citrate and allyl glycolate. All such plasticizers are commercially available from sources such as Aldrich or Sigma Chemical Co. A combination of plasticizers may also be used in the present formulation. The PEG based plasticizers are commercially available or can be made by a variety of methods, such as disclosed in *Poly(ethylene glycol) Chemistry: Biotechnical and Biomedical Applications* (J. M. Harris, Ed.; Plenum Press, NY) the disclosure of which is hereby incorporated by reference.

As used herein, the term "antioxidant" is intended to mean an agent that inhibits oxidation and is thus used to prevent the deterioration of preparations by the oxidative process. Such compounds include, by way of example and without limitation, ascorbic acid, ascorbic palmitate, Vitamin E, Vitamin E derivative, butylated hydroxyanisole, butylated hydroxytoluene, hypophosphorous acid, monothioglycerol, propyl gallate, sodium ascorbate, sodium bisulfite, sodium formaldehyde sulfoxylate, sodium metalbisulfite and other such materials known to those of ordinary skill in the art.

Although not necessary, the formulation of the present invention may include a chelating agent, preservative, adsorbents, acidifying agent, alkalizing agent, antifoaming agent, buffering agent, colorant, electrolyte, flavorant, polishing agent, salt, stabilizer, sweetening agent, tonicity modifier, antiadherent, binder, diluent, direct compression excipient, disintegrant, glidant, lubricant, opaquant, polishing agent, plasticizer, other pharmaceutical excipient, or a combination thereof.

As used herein, the term chelating agent is intended to mean a compound that chelates metal ions in solution. Exemplary chelating agents include EDTA (tetrasodium ethylenediaminetetraacetate), DTPA (pentasodium diethylenetriaminepentaacetate), HEDTA (trisodium salt of N-(hydroxyethyl)-ethylenediaminetriacetic acid), NTA (trisodium nitrilotriacetate), disodium ethanoldiglycine ($Na_2EDG$), sodium diethanolglycine (DEGNa), citric acid, and other compounds known to those of ordinary skill in the art.

As used herein, the term "adsorbent" is intended to mean an agent capable of holding other molecules onto its surface by physical or chemical (chemisorption) means. Such compounds include, by way of example and without limitation, powdered and activated charcoal and other materials known to one of ordinary skill in the art.

As used herein, the term "alkalizing agent" is intended to mean a compound used to provide an alkaline medium. Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, and trolamine and others known to those of ordinary skill in the art.

As used herein, the term "acidifying agent" is intended to mean a compound used to provide an acidic medium. Such compounds include, by way of example and without limitation, acetic acid, amino acid, citric acid, fumaric acid and other alpha hydroxy acids, hydrochloric acid, ascorbic acid, and nitric acid and others known to those of ordinary skill in the art.

As used herein, the term "antiadherent" is intended to mean an agent that prevents the sticking of tablet formulation ingredients to punches and dies in a tableting machine during production. Such compounds include, by way of example and without limitation, magnesium stearate, talc, calcium stearate, glyceryl behenate, polyethylene glycol (PEG), hydrogenated vegetable oil, mineral oil, stearic acid and other materials known to one of ordinary skill in the art.

As used herein, the term "binder" is intended to mean a substance used to cause adhesion of powder particles in granulations. Such compounds include, by way of example and without limitation, acacia, alginic acid, carboxymethylcellulose sodium, poly(vinylpyrrolidone), compressible sugar (e.g., NuTab), ethylcellulose, gelatin, liquid glucose, methylcellulose, povidone and pregelatinized starch and other materials known to one of ordinary skill in the art.

Exemplary binders include acacia, tragacanth, gelatin, starch, cellulose materials such as methyl cellulose and sodium carboxy methyl cellulose, alginic acids and salts thereof, polyethylene glycol, guar gum, polysaccharide, bentonites, sugars, invert sugars, poloxamers (PLURONIC™ F68, PLURONIC™ F127), collagen, albumin, gelatin, cellulosics in nonaqueous solvents, combinations thereof and the like. Other binders include, for example, polypropylene glycol, polyoxyethylene-polypropylene copolymer, polyethylene ester, polyethylene sorbitan ester, polyethylene oxide, combinations thereof and other materials known to one of ordinary skill in the art.

As used herein, the term "antifoaming agent" is intended to mean a compound or compounds that prevents or reduces the amount of foaming that forms on the surface of the fill composition. Suitable antifoaming agents include by way of example and without limitation, dimethicone, SIMETHICONE, octoxynol and others known to those of ordinary skill in the art.

As used herein, the term "buffering agent" is intended to mean a compound used to resist a change in pH upon dilution or addition of acid or alkali. Such compounds include, by way of example and without limitation, potassium metaphosphate, potassium phosphate, monobasic sodium acetate and sodium citrate anhydrous and dehydrate and other such materials known to those of ordinary skill in the art.

As used herein, the term "diluent" or "filler" is intended to mean inert substances used as fillers to create the desired bulk, flow properties, and compression characteristics in the preparation of tablets and capsules. Such compounds include, by way of example and without limitation, dibasic calcium phosphate, kaolin, lactose, sucrose, mannitol, microcrystalline cellulose, powdered cellulose, precipitated calcium carbonate, sorbitol, and starch and other materials known to one of ordinary skill in the art.

As used herein, the term "direct compression excipient" is intended to mean a compound used in direct compression tablet formulations. Such compounds include, by way of example and without limitation, dibasic calcium phosphate (e.g., Ditab) and other materials known to one of ordinary skill in the art.

As used herein, the term "glidant" is intended to mean an agent used in tablet and capsule formulations to promote flowability of the granulation. Such compounds include, by way of example and without limitation, colloidal silica, cornstarch, talc, calcium silicate, magnesium silicate, colloidal silicon, silicon hydrogel and other materials known to one of ordinary skill in the art.

As used herein, the term "lubricant" is intended to mean a substance used in the instant formulations to reduce friction during compression or other processing. Such compounds include, by way of example and without limitation, calcium stearate, magnesium stearate, mineral oil, stearic acid, and zinc stearate and other materials known to one of ordinary skill in the art.

As used herein, the term "opaquant" is intended to mean a compound used to render a capsule or a tablet coating opaque. May be used alone or in combination with a colorant. Such compounds include, by way of example and without limitation, titanium dioxide, talc and other materials known to one of ordinary skill in the art.

As used herein, the term "disintegrant" is intended to mean a compound used in solid dosage forms to promote the disruption of the solid mass into smaller particles that are more readily dispersed or dissolved. Exemplary disintegrants include, by way of example and without limitation, starches such as corn starch, potato starch, pre-gelatinized and modified starches thereof, sweeteners, clays, such as bentonite, microcrystalline cellulose (e.g., Avicel), carboxymethylcellulose calcium, cellulose polyacrilin potassium (e.g., Amberlite), alginates, sodium starch glycolate, gums such as agar, guar, locust bean, karaya, pectin, tragacanth; crospovidone and other materials known to one of ordinary skill in the art.

As used herein, the term "preservative" is intended to mean a compound used to prevent the growth of microorganisms. Such compounds include, by way of example and without limitation, benzalkonium chloride, benzethonium chloride, benzoic acid, benzyl alcohol, cetylpyridinium chloride, chlorobutanol, phenol, phenylethyl alcohol, phenylmercuric nitrate, phenylmercuric acetate, thimerosal, metacresol, myristylgamma picolinium chloride, potassium benzoate, potassium sorbate, sodium benzoate, sodium propionate, sorbic acid, thymol, and methyl, ethyl, propyl, or butyl parabens and others known to those of ordinary skill in the art.

As used herein, the term "polishing agent" is intended to mean a compound used to impart brightness to the surface of dosage forms. Such compounds include, by way of example and without limitation, carnauba wax, white wax, combinations thereof and other such materials known to those of ordinary skill in the art.

As used herein, the term "colorant" is intended to mean a compound used to impart color to pharmaceutical preparations. Such compounds include, by way of example and without limitation, FD&C Red No. 3, FD&C Red No. 20, FD&C Yellow No. 6, FD&C Blue No. 2, FD&C Green No. 5, FD&C Orange No. 5, FD&C Red No. 8, caramel, and iron oxide (black, red, yellow), other FD&C dyes and natural coloring agents such as grape skin extract, beet red powder, betacarotene, annato, carmine, turmeric, paprika, combinations thereof and other such materials known to those of ordinary skill in the art.

As used herein, the term "flavorant" is intended to mean a compound used to impart a pleasant flavor and often odor to a pharmaceutical preparation. Exemplary flavoring agents or flavorants include synthetic flavor oils and flavoring aromatics and/or natural oils, extracts from plants, leaves, flowers, fruits and so forth and combinations thereof. These may also include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Other useful flavors include vanilla, citrus oil, including lemon, orange, grape, lime and grapefruit, and fruit essences, including apple, pear, peach, strawberry, raspberry, cherry, plum, pineapple, apricot and so forth. Flavors, which have been found to be particularly useful, include commercially available orange, grape, cherry and bubble gum flavors and mixtures thereof. The amount of flavoring may depend on a number of factors, including the desired organoleptic effect. Flavors will be present in any amount as desired by the artisan of ordinary skill in the art. Particularly preferred flavors are the grape and cherry flavors and citrus flavors such as orange.

As used herein, the term "stabilizer" is intended to mean a compound used to stabilize a active agent against physical, chemical, or biochemical process that would otherwise reduce the therapeutic activity of the agent. Suitable stabilizers include, by way of example and without limitation, albumin, sialic acid, creatinine, glycine and other amino acids, niacinamide, sodium acetyltryptophonate, zinc oxide, sucrose, glucose, lactose, sorbitol, mannitol, glycerol, polyethylene glycols, sodium caprylate and sodium saccharin and others known to those of ordinary skill in the art.

As used herein, the term "sweetening agent" is intended to mean a compound used to impart sweetness to a preparation. Such compounds include, by way of example and without limitation, aspartame, dextrose, glycerin, mannitol, saccharin sodium, sorbitol, sucrose, fructose, sugar substitute, artificial sweetener, and other such materials known to those of ordinary skill in the art.

As used herein, the term "tonicity modifier" is intended to mean a compound or compounds that can be used to adjust the tonicity of the liquid formulation. Suitable tonicity modifiers include glycerin, lactose, mannitol, dextrose, sodium chloride, sodium sulfate, sorbitol, trehalose and others known to those or ordinary skill in the art.

Plasticizers can also be included to modify the properties and characteristics of the polymers used in a pharmaceutical dosage form. As used herein, the term "plasticizer" includes all compounds capable of plasticizing or softening a polymer or binder used in invention. The plasticizer should be able to lower the melting temperature or glass transition temperature (softening point temperature) of the polymer or binder. Plasticizers, such as low molecular weight PEG, generally broaden the average molecular weight of a polymer in which they are included thereby lowering its glass transition temperature or softening point. Plasticizers also generally reduce the viscosity of a polymer. It is possible the plasticizer will impart some particularly advantageous physical properties to the osmotic device of the invention.

Plasticizers useful in the invention can include, by way of example and without limitation, low molecular weight polymers, oligomers, copolymers, oils, small organic molecules, low molecular weight polyols having aliphatic hydroxyls, ester-type plasticizers, glycol ethers, poly(propylene glycol), multi-block polymers, single block polymers, low molecular weight poly(ethylene glycol), citrate ester-type plasticizers, triacetin, propylene glycol and glycerin. Such plasticizers can also include ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, acetyltributylcitrate, triethyl citrate, acetyl triethyl citrate, tributyl citrate and allyl glycolate. All such plasticizers are commercially available from sources such as Aldrich or Sigma Chemical Co. It is also contemplated and within the scope of the invention, that a combination of plasticizers may be used in the present formulation. The PEG based plasticizers are available commercially or can be made by a variety of methods, such as disclosed in *Poly(ethylene glycol) Chemistry: Biotechnical and Biomedical Applications* (J. M. Harris, Ed.; Plenum Press, NY) the disclosure of which is hereby incorporated by reference.

The composition of the invention can be included in any dosage form. Particular dosage forms include a solid or liquid dosage forms. Exemplary suitable dosage forms include tablet, capsule, pill, caplet, troche, sache, and other such dosage forms known to the artisan of ordinary skill in the pharmaceutical sciences.

Examples 3 and 6 describe an exemplary capsule dosage form. Example 13 describes an exemplary tablet dosage form.

The composition of the invention can also include oils such as fixed oils, peanut oil, sesame oil, cottonseed oil, corn oil and olive oil; fatty acids such as oleic acid, stearic acid and isostearic acid; and fatty acid esters such as ethyl oleate, isopropyl myristate, fatty acid glycerides and acetylated fatty acid glycerides. The composition can also include alcohol such as ethanol, isopropanol, hexadecyl alcohol, glycerol and propylene glycol; glycerol ketals such as 2,2-dimethyl-1,3-dioxolane-4-methanol; ethers such as poly(ethylene glycol) 450; petroleum hydrocarbons such as mineral oil and petrolatum; water; a pharmaceutically suitable surfactant, suspending agent or emulsifying agent; or mixtures thereof.

It should be understood that the compounds used in the art of pharmaceutical formulation generally serve a variety of functions or purposes. Thus, if a compound named herein is mentioned only once or is used to define more than one term herein, its purpose or function should not be construed as being limited solely to that named purpose(s) or function(s).

As used herein, the term "oleandrin" is taken to mean all known forms of oleandrin unless otherwise specified. Oleandrin can be present in racemic, optically pure or optically enriched form. *Nerium oleander* plant material can be obtained from commercial plant suppliers such as Aldridge Nursery, Atascosa, Tex.

One or more of the components of the formulation can be present in its free base or pharmaceutically acceptable salt form. As used herein, "pharmaceutically acceptable salt" refers to a compound that has been modified by reacting it with an acid as needed to form an ionically bound pair. Examples of pharmaceutically acceptable salts include conventional non-toxic salts formed, for example, from non-toxic inorganic or organic acids. Suitable non-toxic salts include those derived from inorganic acids such as hydrochloric, hydrobromic, sulfuric, sulfonic, sulfamic, phosphoric, nitric and others known to those of ordinary skill in the art. The salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and others known to those of ordinary skill in the art. Lists of other suitable salts are found in *Remington's Pharmaceutical Sciences*, 17th. ed., Mack Publishing Company, Easton, Pa., 1985, p. 1418, the relevant disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with tissues of human beings and animals and without excessive toxicity, irritation, allergic response, or any other problem or complication, commensurate with a reasonable benefit/risk ratio.

The amount of oleandrin incorporated in a unit dose of the invention will be at least one or more dosage forms and can be selected according to known principles of pharmacy. An effective amount of therapeutic compound is specifically contemplated. By the term "effective amount", it is understood that, with respect to, for example, pharmaceuticals, a pharmaceutically effective amount is contemplated. A pharmaceutically effective amount is the amount or quantity of tramadol which is enough for the required or desired therapeutic response, or in other words, the amount, which is sufficient to elicit an appreciable biological response when, administered to a patient. The appreciable biological response may occur as a result of administration of single or multiple unit doses of an active substance. A unit dose may comprise one or more dosage forms, such as capsules. It will be understood that the specific dose level for any patient will depend upon a variety of factors including the indication being treated, severity of the indication, patient health, age, sex, weight, diet, pharmacological response, the specific dosage form employed and other such factors.

The dose of SCF extract will depend upon the concentration of therapeutically effective components therein. The in vitro cellular assays disclosed herein can be used to determine the relative potency of the extract. The desired dose for oral administration is up to 5 dosage forms although as few as one and as many as ten dosage forms may be administered. Exemplary dosage forms contain 38.5 mg of the SCF extract per dosage form, for a total 38.5 to 385 mg of extract or of cardiac glycoside (1 to 10 dosage forms) per dose.

The oleandrin is present in the dosage form in an amount sufficient to provide a subject with an initial dose of oleandrin of 0.5 to 5 mg. Some embodiments of the dosage form are not enteric coated and release their charge of oleandrin within a period of 0.5 to 1 hours or less. Some embodiments of the dosage form are enteric coated and release their charge of oleandrin downstream of the stomach, such as from the jejunum, ileum, small intestine, and/or large intestine (colon). Oleandrin from enterically coated dosage forms will be released into systemic circulation within 2-3 hr after oral administration. Based on preliminary animal dosing data it is anticipated that 50 to 75% of an administered dose of oleander extract will be orally bioavailable therefore providing 0.25 to 0.4 mg oleandrin per dosage form. Given an average blood volume in adult humans of 5 liters, the anticipated oleandrin plasma concentration will be in the range of 0.05 to 2 ug/ml.

The recommended daily dose of oleandrin, present in the SCF extract, is generally about 0.9 to 5 mg twice daily or about every 12 hours, with a maximum dose of about 1.8 to 10 mg/day.

If desired, the dosage form of the invention can be coated with a finish coating as is commonly done in the art to provide the desired shine, color, taste or other aesthetic characteristics. Materials suitable for preparing the finish coating are well known to those of ordinary skill in the art.

Figure 2:
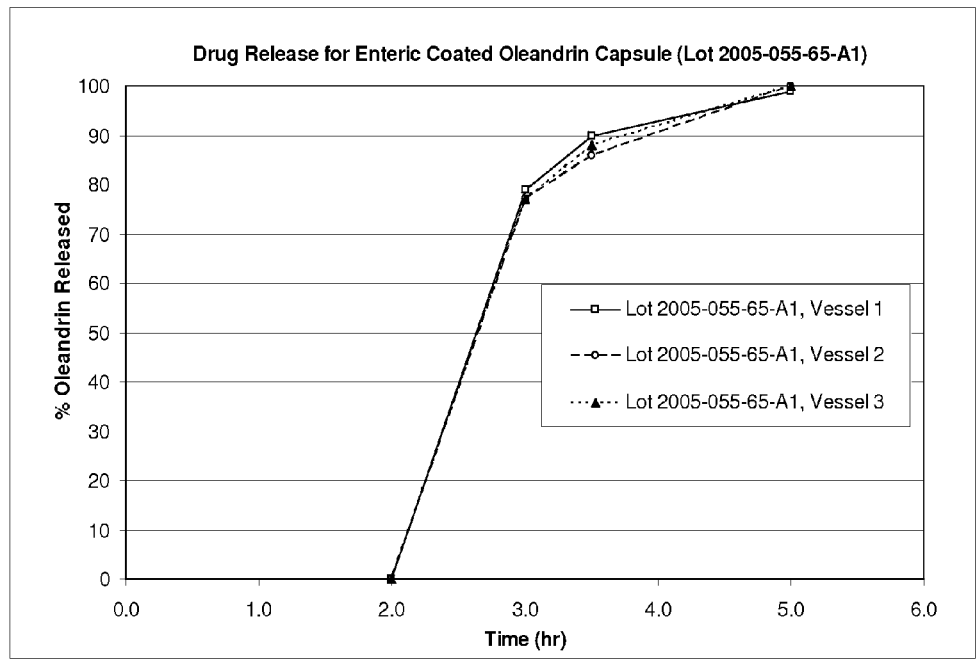
FIG. 2 depicts a dissolution profile for an enteric coated liquid-filled capsule of the invention.

The in vitro release profile of an enteric coated capsule (coated according to Example 6) containing Formulation #2 or Formulation #3 was evaluated according to the USP dissolution method for enteric coated dosage forms. The dissolution profile is depicted in FIG. 2. The USP paddle method was used for the dissolution testing with the paddle speed set at 50 rpm. In the first two hours, 750 mL of 0.1 N hydrochloric acid solution was used as the dissolution medium. After 2 hours, 250 mM sodium phosphate solution was added into 750 mL 0.1 N hydrochloric acid solution to adjust pH to 6.8. The results indicate that less than 5% drug was released in the acid stage and greater than 75% of drug was released within one hour following the adjustment in the dissolution medium In view of the above description and the examples below, one of ordinary skill in the art will be able to practice the invention as claimed without undue experimentation. The foregoing will be better understood with reference to the following examples that detail certain procedures for the preparation of embodiments of the present invention. All references made to these examples are for the purposes of illustration. The following examples should not be considered exhaustive, but merely illustrative of only a few of the many embodiments contemplated by the present invention.

EXAMPLE 1

Supercritical Fluid Extraction of Powdered Oleander Leaves

Method A. with Carbon Dioxide.

Powdered oleander leaves were prepared by harvesting, washing, and drying oleander leaf material, then passing the oleander leaf material through a comminuting and dehydrating apparatus such as those described in U.S. Pat. Nos. 5,236,132, 5,598,979, 6,517,015, and 6,715,705. The weight of the starting material used was 3.94 kg.

The starting material was combined with pure $CO_2$ at a pressure of 300 bar (30 MPa, 4351 psi) and a temperature of 50° C. (122° F.) in an extractor device. A total of 197 kg of $CO_2$ was used, to give a solvent to raw material ratio of 50:1. The mixture of $CO_2$ and raw material was then passed through a separator device, which changed the pressure and temperature of the mixture and separated the extract from the carbon dioxide.

The extract (65 g) was obtained as a brownish, sticky, viscous material having a nice fragrance. The color was likely caused by chlorophyll and other residual chromophoric compounds. For an exact yield determination, the tubes and separator were rinsed out with acetone and the acetone was evaporated to give an addition 9 g of extract. The total extract amount was 74 g. Based on the weight of the starting material, the yield of the extract was 1.88%. The content of oleandrin in the extract was calculated using high pressure liquid chromatography and mass spectrometry to be 560.1 mg, or a yield of 0.76%.

Method B. with Mixture of Carbon Dioxide and Ethanol

Powdered oleander leaves were prepared by harvesting, washing, and drying oleander leaf material, then passing the oleander leaf material through a comminuting and dehydrating apparatus such as those described in U.S. Pat. Nos. 5,236,132, 5,598,979, 6,517,015, and 6,715,705. The weight of the starting material used was 3.85 kg.

The starting material was combined with pure $CO_2$ and 5% ethanol as a modifier at a pressure of 280 bar (28 MPa, 4061 psi) and a temperature of 50° C. (122° F.) in an extractor device. A total of 160 kg of $CO_2$ and 8 kg ethanol was used, to give a solvent to raw material ratio of 43.6 to 1. The mixture of $CO_2$, ethanol, and raw material was then passed through a separator device, which changed the pressure and temperature of the mixture and separated the extract from the carbon dioxide.

The extract (207 g) was obtained after the removal of ethanol as a dark green, sticky, viscous mass obviously containing some chlorophyll. Based on the weight of the starting material, the yield of the extract was 5.38%. The content of oleandrin in the extract was calculated using high pressure liquid chromatography and mass spectrometry to be 1.89 g, or a yield of 0.91%.

EXAMPLE 2

Hot-Water Extraction of Powdered Oleander Leaves

Comparative Example

Hot water extraction is typically used to extract oleandrin and other active components from oleander leaves. Examples of hot water extraction processes can be found in U.S. Pat. Nos. 5,135,745 and 5,869,060.

A hot water extraction was carried out using 5 g of powdered oleander leaves. Ten volumes of boiling water (by weight of the oleander starting material) were added to the powdered oleander leaves and the mixture was stirred constantly for 6 hours. The mixture was then filtered and the leaf residue was collected and extracted again under the same conditions. The filtrates were combined and lyophilized. The appearance of the extract was brown. The dried extract material weighed about 1.44 g. 34.21 mg of the extract material was dissolved in water and subjected to oleandrin content analysis using high pressure liquid chromatography and mass spectrometry. The amount of oleandrin was determined to be 3.68 mg. The oleandrin yield, based on the amount of extract, was calculated to be 0.26%. The Table 1 below shows a comparison between the oleandrin yields for the two supercritical carbon dioxide extractions of Example 1 and the hot water extraction.

TABLE 1

Comparison of Yields

| Extraction Medium | Oleandrin yield based on total extract weight |
|---|---|
| Supercritical Carbon Dioxide: Example 1, Method A | 0.76% |
| Supercritical Carbon Dioxide: Example 1, Method B | 0.91% |
| Hot Water Extraction: Example 2 | 0.26% |

EXAMPLE 3

Preparation of Pharmaceutical Compositions

In each of the following methods, the SCF extract contained about 25 mg of oleandrin per gram of extract.

Method A. Cremophor-Based Drug Delivery System

The following ingredients were provided in the amounts indicated.

| Reagent Name | Function | Percent of Formulation (% w/w) |
|---|---|---|
| SCF extract | Active agent | 3.7 |
| Vitamin E | Antioxidant | 0.1 |
| Labrasol | Surfactant | 9.2 |
| Ethanol | Co-solvent | 9.6 |
| Cremophor EL | Surfactant | 62.6 |
| Cremophor RH40 | Surfactant | 14.7 |

The excipients were dispensed into a jar and shook in a New Brunswick Scientific C24KC Refrigerated Incubator shaker for 24 hours at 60° C. to ensure homogeneity. The samples were then pulled and visually inspected for solubilization. Both the API and remainder of the extract were totally dissolved for all formulations after 24 hours.

Method B. GMO/Cremophor-Based Drug Delivery System

The following ingredients were provided in the amounts indicated.

| Reagent Name | Function | Percent of Formulation (% w/w) |
| --- | --- | --- |
| SCF extract | Active agent | 4.7 |
| Vitamin E | Antioxidant | 0.1 |
| Labrasol | Surfactant | 8.5 |
| Ethanol | Co-solvent | 7.6 |
| Cremophor EL | Surfactant | 56.1 |
| Glycerol Monooleate | Surfactant | 23.2 |

The procedure of Method A was followed.

Method C. Labrasol-Based Drug Delivery System

The following ingredients were provided in the amounts indicated.

| Reagent Name | Function | Percent of Formulation (% w/w) |
| --- | --- | --- |
| SCF extract | Active agent | 3.7 |
| Vitamin E | Antioxidant | 0.1 |
| Labrasol | Surfactant | 86.6 |
| Ethanol | Co-solvent | 9.6 |

The procedure of Method A was followed.

Method D. Vitamin E-TPGS Based Micelle Forming System

The following ingredients were provided in the amounts indicated.

| Component | Function | Weight % (w/w) |
| --- | --- | --- |
| Vitamin E | Antioxidant | 1.0 |
| Vitamin E TPGS | Surfactant | 95.2 |
| SCF extract | Active agent | 3.8 |

The procedure of Method A was followed.

Method E. Multi-Component Drug Delivery System

The following ingredients were provided in the amounts indicated.

| Component | Weight (g) | Weight % (w/w) |
| --- | --- | --- |
| Vitamin E | 10.0 | 1.0 |
| Cremophor ELP | 580.4 | 55.9 |
| Labrasol | 89.0 | 8.6 |
| Glycerol Monooleate | 241.0 | 23.2 |
| Ethanol | 80.0 | 7.7 |
| SCF extract | 38.5 | 3.7 |
| Total | 1038.9 | 100 |

The procedure of Method A was followed.

EXAMPLE 4

In Vitro Dissolution Assay

Method A. Screening Studies to Identify Materials Suitable for the Solubilizer

A screening assay was conducted to determine which materials might be suitable for use in the liquid composition. Preliminary solubility studies were performed by preparing binary mixtures containing an excipient and the SCF extract. A suitable single excipient solubilizes a major portion of the oleandrin and other components present in the extract.

The SCF extract was placed in the solubilizer at a concentration of 77 mg SCF extract per mL of excipient in 20 mL scintillation vials. After weighing out the solubilizer and extract in the vials, the samples were mixed using a vortex mixer. Those samples that did not go into solution after being vortexed at ambient conditions were heated in a hot water bath at 100° C. for 15 minutes, vortexed, sonicated for 10 minutes, and then reheated for another 15 minutes at 100° C. The samples were then cooled to ambient condition for 24 hours and visually inspected for the presence of particles.

Exemplary suitable water soluble solvents included: ethanol, Lauroglycol 90, Pharmasolve, Soluphor P and Triacetin.

Exemplary water insoluble solvent included: Captex 350, Captex 355, glyceryl monooleate, Miglyol 810, olive oil, sesame oil, and Softisan 645, Exemplary surfactants included: Cremophor EL, Cremophor RH40, Gelucire 33/01, Gelucire 43/01, Gelucire 44/14, Gelucire 50/13, labrafil M 1944, labrafil M 2125, labrasol, lutrol L44 NF, plurol oleique, span 20, span 80 and Tween 80.

Method B. Screening Studies to Identify Solubilizer Suitable for Use in the Liquid Compostion A screening assay was conducted to determine which materials might be suitable for use as a solubilizer in the liquid composition. A suitable solubilizer was able to dissolve the SCF extract to make a clear liquid composition.

Method C. Dissolution Assay to Evaluate Performance of Solubilizer

An aliquot (one to a few drops) of liquid composition containing SCF extract and solubilizer was placed in 200 ml of phosphate buffer (pH 6.8, 50 mM) with stirring at ambient temperature. The clarity of the solution was then determined.

EXAMPLE 5

Determination of Clarity

Method A. Visual Inspection with the Unaided Eye

A vial containing the sample being analyzed was held up to a light source. The presence of suspended solids was determined visually.

Method B. Visual Inspection with a Microscope

An aliquot of liquid composition was placed on a microscope slide and viewed under 1000× magnification. The presence of suspended solids was determined visually.

EXAMPLE 6

Preparation of Enteric Coated Capsules

Step I: Preparation of Liquid-Filled Capsule

Hard gelatin capsules (50 counts, 00 size) were filled with a liquid composition of Example 3. These capsules were manually filled with 800 mg of the formulation and then sealed by hand with a 50% ethanol/50% water solution. The capsules were then banded by hand with 22% gelatin solution containing the following ingredients in the amounts indicated.

| Ingredient | Wt. (g) |
| --- | --- |
| Gelatin | 140.0 |
| Polysorbate 80 | 6.0 |
| Water | 454.0 |
| Total | 650.0 |

The gelatin solution mixed thoroughly and allowed to swell for 1-2 hours. After the swelling period, the solution was covered tightly and placed in a 55° C. oven and allowed to liquefy. Once the entire gelatin solution was liquid, the banding was performed Using a pointed round 3/0 artist brush, the gelatin solution was painted onto the capsules. Banding kit provided by Shionogi was used. After the banding, the capsules were kept at ambient conditions for 12 hours to allow the band to cure.

Step II: Coating of Liquid-Filled Capsule

A coating dispersion was prepared from the ingredients listed in the table below.

| Ingredient | Wt. % | Solids % | Solids (g) | g/Batch |
| --- | --- | --- | --- | --- |
| Eudragit L30D55 | 40.4 | 60.5 | 76.5 | 254.9 |
| TEC | 1.8 | 9.0 | 11.4 | 11.4 |
| AlTalc 500V | 6.1 | 30.5 | 38.5 | 38.5 |
| Water | 51.7 | | | 326.2 |
| Total | 100.0 | 100.0 | 126.4 | 631.0 |

If banded capsules according to Step I were used, the dispersion was applied to the capsules to a 20.0 mg/cm² coating level. The following conditions were used to coat the capsules.

| Parameters | Set-up |
| --- | --- |
| Coating Equipment | Vector LDCS-3 |
| Batch Size | 500 g |
| Inlet Air Temp. | 40° C. |
| Exhaust Air Temp. | 27-30° C. |
| Inlet Air Volume | 20-25 CFM |
| Pan Speed | 20 rpm |
| Pump Speed | 9 rpm (3.5 to 4.0 g/min) |
| Nozzle Pressure | 15 psi |
| Nozzle diameter | 1.0 mm |
| Distance from tablet bed* | 2-3 in |

*Spray nozzle was set such that both the nozzle and spray path were under the flow path of inlet air.

EXAMPLE 7

Treatment of Skin Related Diseases Such as Cancers Including but not Limited to Prevention of Treatment of Melanoma, Basal Cell Carcinoma, and Squamous Cell Carcinoma as Well as Noncancerous Inflammatory Skin Diseases Including but not Limited to Actinic Keratosis, Psoriasis, and Eczema The SCF extract is administered to a subject suffering from malignant or nonmalignant proliferative skin diseases such as those cited above. The SCF extract is administered as a cream or ointment or contained within a dermal patch containing 0.01 mg to 10 mg of SCF extract per unit dose. The subject is administered a unit dose up to three times daily for a period of 1 to 14 days or until the skin diseases is in remission. It is expected that such treatment will significantly lessen or eliminate the inflammation and malignant processes leading to a progression of the disease. The subject should experience a reduction in the severity of the dermal lesion(s) and the eventual resolution of the dermatologic disease itself. Malignant diseases should be expected to be reduced in rate of growth or inhibited from increase in severity of the disease. Actual regression of established malignant lesions may be expected.

EXAMPLE 8

Prevention of Skin Related Diseases Such as Skin Cancers

The SCF extract is administered to a subject suffering from a predisposition to formation of skin cancer such as those frequently exposed to ultraviolet light (from sunlight) or carcinogens from chemicals. The SCF extract is administered as a cream or ointment or contained within a dermal patch containing 0.01 to 10 mg of SCF extract per unit dose. The subject is administered a unit dose up to three times daily every time exposure to a carcinogen promoting event is anticipated (exposure to sunlight). Such administration could, for example, be made as a sunscreen for blocking sunlight UV exposure and SCF extract for prevention of tumor induction in dermal tissue. It would be expected that such a use of the SCE in a dermal product would block formation and/or promotion of malignant skin disease or nonmalignant skin disorders where proliferation leads to a worsening of the disease process (e.g. acktinic keratosis, psoriasis and/or eczema).

EXAMPLE 9

Treatment of Solid Tumors in Humans or Other Vertebrate Animals

SCF extract can be used to treat cancers of the rectum, anus, colorectal tissues, head and neck tissues, esophageal tissue, lung (both non small cell and small cell carcinomas), breast, stomach, pancreas, prostate, liver, kidney, bladder, ureter, ovarian tissue, carcinoid tumors, sarcomas of bone, mesothelioma, and neoplasms of the central nervous system.

The SCF extract is administered to a subject suffering from solid malignant diseases such as those mentioned above. The SCF extract is administered as an oral dosage form containing 1 to 50 mg of SCF extract per unit dose. The subject is administered a unit dose up to twice daily times daily for a period of 28 days/cycle of treatment. Up to three cycles of treatment may be required. The subject should experience tumor growth to either slow in rate of proliferation or to regress. Completion resolution of the tumor may occur. The therapy with SCF extract may be used as a sole agent or combined with cytotoxic chemotherapy or radiation treatment or may be combined with appropriate immunotherapy without causing undue interference with the desired antitumor effect of conventional therapy.

EXAMPLE 10

Comparison of Cytotoxicity of Hot Water Extract of *Nerium oleander* to an SCF Extract Made Using Supercritical $CO_2$ in Two Human Tumor Cell Lines The cytotoxic potential of both extracts are compared directly with that of oleandrin. The samples contained the same amounts of oleandrin even though their concentration of oleandrin differed due to the concentration of oleandrin present in the extracts.

BRO (human melanoma) and Panc-1 (human pancreatic cancer) cells ($8\times10^3$/well) were plated in a 96 well plate and allowed to attach overnight. Drug or extracts were then added to the cells. After 72 hr of incubation, relative cell proliferation (relative to control untreated cells) was assessed by crystal violet staining method.

EXAMPLE 11

HPLC Analysis of Solutions Containing Oleandrin

Samples (oleandrin standard, SCF extract and hot-water extract) were analyzed on HPLC (Waters) using the following conditions: Symmetry C18 column (5.0 μm, 150×4.6 mm I.D.; Waters); Mobile phase of MeOH:water=54:46 (v/v) and flow rate at 1.0 ml/min. Detection wavelength was set at 217 nm. The samples were prepared by dissolving the compound or extract in a fixed amount of HPLC solvent to achieve an approximate target concentration of oleandrin.

EXAMPLE 12

Evaluation of Anti-Viral Activity of an SCF Extract

The test consists of determining the relative ability of oleander extract or a positive control (AZT) to inhibit proliferation of the ROJO strain of HIV-1 in human peripheral blood mononuclear cells (PBMCs). Infected cells are exposed to the drug or extract for 48 hr. The test is used to determine the IC50 of oleander extract (that concentration of extract producing a 50% inhibition of viral proliferation) versus that concentration of extract capable of killing the human PBMC. This is, in effect, a determination of the therapeutic index of the extract. This is essentially a determination of whether or not the extract can kill HIV-1 without killing the PBMC cell itself.

One should observe an IC50 against viral proliferation of about 5.0 ug/ml or less while the concentration required to kill cells should not have been reached even at concentrations as high as 100 ug/ml. The data obtained suggest that oleander extract should be useful in terms of inhibiting HIV-1 viral proliferation harbored within PBMC cells.

EXAMPLE 13

Preparation of a Tablet Comprising SCF Extract

An initial tabletting mixture of 3% Syloid 244FP and 97% microcrystalline cellulose (MCC) was mixed. Then, an existing batch of composition prepared according to Example 3 was incorporated into the Syloid/MCC mixture via wet granulation. This mixture is labeled "Initial Tabletting Mixture) in the table below. Additional MCC was added extragranularly to increase compressibility. This addition to the Initial Tabletting Mixture was labeled as "Extra-granular Addition." The resultant mixture from the extra-granular addition was the same composition as the "Final Tabletting Mixture."

| Component | Weight (g) | Weight % (w/w) |
|---|---|---|
| Initial Tabletting Mixture | | |
| Microcrystalline cellulose | 48.5 | 74.2 |
| Colloidal Silicon Dioxide/Syloid 244FP | 1.5 | 2.3 |
| Formulation from Ex. 3 | 15.351 | 23.5 |
| Total | 65.351 | 100.0 |
| Extragranular addition | | |
| Initial Tabulating Mixture | 2.5 | 50.0 |
| Microcrystalline cellulose | 2.5 | 50.0 |
| Total | 5 | 100.0 |
| Final Tabletting Mixture: Abbreviated | | |
| Microcrystalline cellulose | 4.36 | 87.11 |
| Colloidal Silicon Dioxide/Syloid 244FP | 0.06 | 1.15 |
| Formulation from Ex. 3 | 0.59 | 11.75 |
| Total | 5.00 | 100 |
| Final Tabletting Mixture: Detailed | | |
| Microcrystalline cellulose | 4.36 | 87.11 |
| Colloidal Silicon Dioxide/Syloid 244FP | 0.06 | 1.15 |
| Vitamin E | 0.01 | 0.11 |
| Cremophor ELP | 0.33 | 6.56 |
| Labrasol | 0.05 | 1.01 |
| Glycerol Monooleate | 0.14 | 2.72 |
| Ethanol | 0.05 | 0.90 |
| SCF extract | 0.02 | 0.44 |
| Total | 5.00 | 100.00 |

Syloid 244FP is a colloidal silicon dioxide manufactured by Grace Davison. Colloidal silicon dioxide is commonly used to provide several functions, such as an adsorbant, glidant, and tablet disintegrant. Syloid 244FP was chosen for its ability to adsorb 3 times its weight in oil and for its 5.5 micron particle size.

EXAMPLE 14

HPLC Carbohydrate Analysis

Carbohydrate content in oleander extracts was determined using the method of Yemm and Willis (The Estimation of Carbohydrates in Plant Extracts by Anthrone, 1954, 57:508-514). Briefly, aliquots of plant extracts were added to a tube containing anthrone solution (0.2 g anthrone dissolved in 100 ml $H_2SO_4$) and chilled on ice. The resulting color was read in a spectrophotometer at 625 nm using a 1 cm cell. A standard curve consisting of serial dilutions of glucose was used to quantify the results. Other sugars such as fructose, arabinose and rhamnose also react with the anthrone solution and thus this method is a measure of many carbohydrates in the plant extract.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

The invention claimed is:

1. A pharmaceutical composition comprising:
a supercritical fluid extract of *Nerium* species comprising oleandrin and at least one other supercritical fluid extractable pharmacologically active agent obtained by way of the supercritical fluid extraction, wherein the extract comprises less than 0.5% by weight polysaccharide; and
an extract-solubilizing amount of at least one solubilizer.

2. The composition of claim 1, wherein the pharmaceutical composition comprises:
a supercritical fluid extract of *Nerium* species; and
an extract-solubilizing amount of solubilizer comprising at least one component selected from the group consisting of water soluble (miscible) co-solvent, water insoluble (immiscible) co-solvent, antioxidant, and surfactant.

3. The composition of claim 2, wherein the pharmaceutical composition comprises:
a supercritical fluid extract of *Nerium* species; and
an extract-solubilizing amount of solubilizer comprising at least three components selected from the group consisting of water soluble (miscible) co-solvent, water insoluble (immiscible) co-solvent, antioxidant, and surfactant.

4. The composition of claim 3, wherein the surfactant is selected from the group of solubilizing agent, emulsifying agent, and a combination thereof.

5. The composition of claim 4, wherein the pharmaceutical composition comprises:
a supercritical fluid extract of *Nerium* species;
at least one water miscible solvent;
at least one antioxidant; and
at least one solubilizing agent.

6. The composition of claim 1, wherein the *Nerium* species is *Nerium oleander*, and the extract comprises oleandrin.

7. The composition of claim 6, wherein the at least one water miscible solvent is selected from the group consisting of glycol, alcohol, and poly(ethylene glycol).

8. The composition of claim 6, wherein the at least one solubilizing agent is a surfactant selected from the group consisting of a pegylated surfactant, vitamin E-TPGS, chremophor, labrasol, labrafil, poloxamer.

9. The composition of claim 6, wherein the at least one antioxidant is selected from the group consisting of Vitamin E, BHT, vitamin C palmitate.

10. The composition of claim 6 further comprising at least one emulsifying agent.

11. The composition of claim 10, wherein the at least one emulsifying agent is selected from the group consisting of Vitamin E-TPGS, chremophor, labrafil, labrasol, poloxamer.

12. The composition of claim 10 further comprising at least one water immiscible solvent.

13. The composition of claim 12, wherein the at least one water immiscible solvent is selected from the group consisting of glycerol monooleate, triglycerides, oleic acid, and combinations thereof.

14. The composition of claim 6 further comprising at least one water immiscible solvent.

15. The composition of claim 13, wherein the at least one water immiscible solvent is selected from the group consisting of glycerol monooleate, triglycerides, oleic acid, and combinations thereof.

16. The composition of clam 6, wherein the composition is anhydrous or comprises only endogenous water.

17. A capsule formulation comprising a capsule shell, and a pharmaceutical composition according to claim 1.

18. The formulation of claim 17 further comprising an enteric coating exterior to and surrounding the capsule.

19. The formulation of claim 18, wherein the enteric coating comprises a polymer soluble or erodible in water at a pH of 5 or greater.

20. A pharmaceutical dosage form comprising the composition of claim 1.

21. The composition of claim 1, wherein the supercritical fluid extract has been prepared by a supercritical fluid extraction process comprising:
treating a cardiac glycoside-containing *Nerium* species plant mass with a supercritical fluid for a period of time sufficient to extract the cardiac glycoside from the plant mass;
separating the plant mass from the supercritical fluid; and removing the supercritical fluid thereby forming a supercritical fluid extract comprising cardiac glycoside.

22. The composition of claim 1, wherein the at least one other supercritical fluid extractable pharmacologically active agent is selected from the group consisting of oleandrigenin, ursolic acid, betulinic acid, odoroside, neritaloside, oleanolic acid and one or more triterpenes.

23. The composition of claim 1, wherein the SCF extract comprises less than 0.01% by weight polysaccharide.

24. The composition of claim 22, wherein the SCF extract further comprises one or more compounds selected from the group consisting of neritaloside; oleanolic acid; ursolic acid; betulinic acid; betulin (urs-12-ene-3β,28-diol); 28-norurs-12-en-3β-ol; urs-12-en-3β-ol; 3β,3β-hydroxy-12-oleanen-28-oic acid; 3β,20α-dihydroxyurs-21-en-38-oic acid; 3β,27-dihydroxy-12-ursen-38-oic acid; 3β,13β-dihydroxyurs-11-en-28-oic acid; 3β,12α-dihydroxyoleanan-28,13β-olide; and 3β,27-dihydroxy-12-oleanan-28-oic acid.

25. The composition of claim 1, wherein the SCF extract comprises one or more cardiac glycosides and one or more cardiac glycoside precursors.

26. The composition of claim 25, wherein the one or more cardiac glycoside precursors is selected from the group consisting of an aglycone constituent of a cardiac glycoside and a glycone constituent of a cardiac glycoside.

27. The composition claim 26, wherein:
the aglycone is selected from the group consisting of oleandrigenin, digitoxin, acetyl digitoxins, digitoxigenin, digoxin, acetyl digoxins, digoxigenin, medigoxin, strophanthins, cymarine, ouabain, strophanthidin; and
the glycone is selected from the group consisting of glucoside, fructoside, and glucuronide.

28. The composition of claim 27 further comprising one or more of neritaloside; oleanolic acid; ursolic acid; betulinic acid; betulin (urs-12-ene-3β,28-diol); 28-norurs-12-en-3β-ol; urs-12-en-3β-ol; 3β,3β-hydroxy-12-oleanen-28-oic acid; 3β,20α-dihydroxyurs-21-en-38-oic acid; 3β,27-dihydroxy-12-ursen-38-oic acid; 3β,13β-dihydroxyurs-11-en-28-oic acid; 3β,12α-dihydroxyoleanan-28,13β-olide; and 3β,27-dihydroxy-12-oleanan-28-oic acid.

29. The composition of claim 25, wherein the SCF extract comprises one or more cardiac glycosides selected from the group consisting of Apocannoside, cymarin, Calotropin, 16α-acetoxycalotropin, 15β-hydroxycalotropin, calactin, 15β-hydroxycalactin, asclepin, 16α-hydroxyasclepin, uscharidin, uscharin, uzarigenin, Digitoxigenin, oleandrigenin, digitoxigenin, α-L-cymaroside, digitoxigenin β-gentiobiosyl-α-L-cymaroside, $\Delta^{16}$-digitoxigenin β-D-glucosyl-α-L-cymaroside, Calotropin, calactin, uscharin, voruscharin, 2''-oxovoruscharin, 2'-O-Acetyl cerleaside A, 17α-neriifolin, 17β-neriifolin, cerberin, Hyrcanoside, Securigenin-3β-O-β-6-deoxyguloside, 19-hydroxy-sarmentogenin-3β-O-β-6-deoxyguloside, sarmentogenin-3β-O-[α-allosyl-(1→4)-β-6-deoxyalloside], securigenin-3β-O-[α-allosyl-(1→4)-β-6-deoxyalloside], Digoxin, digitoxin, gitoxin, Elaeodendrosides, Acovenosigenin A 3-O-α-L-ramnopyranoside, euonymoside A, euonymusoside A, Euonymoside A, Maquiroside A, Oleander, oleandrin, cardenolide N-1, cardenolide N-4, 3β-O-(β-D-sarmentosyl)-16β-acetoxy-14-hydroxy-5β,14β-card-20-(22)-enolide, 16β-acetoxy-3β,14-dihydroxy-5β,14β-card-20-(22)-enolide, 17-epi-11α-hydroxy-6,7-dehydrostrophanthidin-3-O-β-boivinopyranoside, 6,7-dehydrostrophanthidin-3-O-β-boivinopyranoside, 6,7-dehydrostrophanthidin-3-O-β-oleandropyranoside, Convallatoxin, 3'-O-β-D-glucopyranosylcalactin, 12-dehydroxyghalakinoside, 6'-dehydroxyghala-kinoside, ghalakinoside, calactin, Periplocin isomers, Rhodexin A, 3-O-β-D-fucopyranosylstrophanthidin, 3-O-β-D-quinovopyranosylperiplogenin, 3-O-β-D-glucopyranosyl-(1→4)-α-L-rhamnopyranosylcannogenin, 3-O-β-D-xylopyranosylperiplogenin, 3-O-β-D-quinovopyranosylstrophanthidin, 3-O-β-D-xylopyranosylstrophanthidin, 3-O-β-D-fucopyranosylperiplogenin, 3-O-α-L-rhamnopyranosylcannogenol, convallatoxin, 3-O-α-L-rhamnpyranosylacovenosigenin A, Stebloside, mansonin, Periplogenin digitoxoside, Periplocymarin, digitoxigenin 3-O—[O-β-D-glucopyranosyl-(1→6)-O-β-D-glucopyranosyl-(1→4)-β-D-digitoxopyranoside, echujin, corchorusoside C, 3-O-(β-glucopyranosyl)acovenosigenin A, Ouabain, Neriifolin, 3'-O-methylevomonoside, 2' acetylneriifolin, Thevetin A and B, thevetoside, Proscillaridin A, and scillaren A.

30. A method of treating a disease or disorder therapeutically responsive to cardiac glycoside therapy in a subject in need thereof, the method comprising administering to the subject a formulation according to claim 20.

* * * * *